United States Patent [19]

Welch, Jr.

[11] 4,267,331
[45] May 12, 1981

[54] PROCESS FOR THE PRODUCTION OF 2-SUBSTITUTED PYRIDO[4,3-B]-INDOLES

[75] Inventor: Willard M. Welch, Jr., Mystic, Conn.

[73] Assignee: Pfizer Inc., New York, N.Y.

[21] Appl. No.: 112,189

[22] Filed: Jan. 15, 1980

Related U.S. Application Data

[60] Division of Ser. No. 5,698, Jan. 23, 1979, which is a continuation-in-part of Ser. No. 799,392, May 23, 1977, abandoned.

[51] Int. Cl.³ .......................................... C07D 471/04
[52] U.S. Cl. .................................................... 546/85
[58] Field of Search ........................................ 546/85

[56] References Cited

U.S. PATENT DOCUMENTS

| | | | |
|---|---|---|---|
| 3,382,250 | 5/1968 | Johnson et al. | 546/85 |
| 3,687,961 | 8/1972 | Bernstein et al. | 546/85 |
| 3,983,239 | 9/1976 | Nagai et al. | 424/267 |
| 3,991,199 | 11/1976 | Berger | 546/85 |
| 4,001,263 | 1/1977 | Plattner et al. | 546/85 |
| 4,141,980 | 2/1979 | Berger | 546/85 |

OTHER PUBLICATIONS

Colonge et al., Bull. Soc. Chim. France, 1966, pp. 2005–2011.

*Primary Examiner*—Henry R. Jiles
*Assistant Examiner*—Natalia Harkaway
*Attorney, Agent, or Firm*—Connolly and Hutz

[57] ABSTRACT

A process for production of certain 2-substituted-5-aryl-2,3,4,4a,5,9b-hexahydro-1H-pyrido[4,3-b]indole tranquilizing agents of the formula

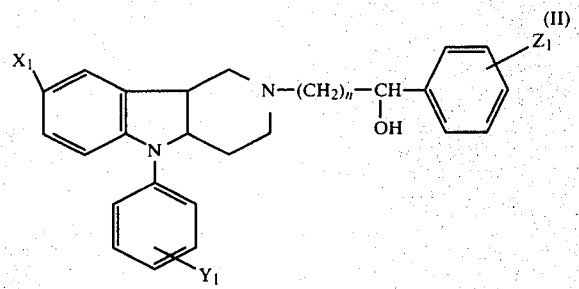

wherein $X_1$ and $Y_1$ are each hydrogen or fluoro; $Z_1$ is hydrogen, fluoro or methoxy and n is 3 or 4 which comprises contacting an amine of the formula

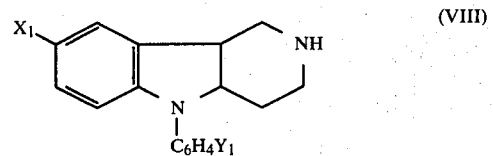

with an equimolar amount of a lactol of the formula

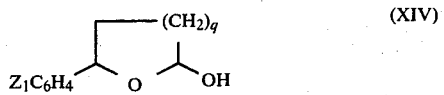

wherein q is 1 or 2; in the presence of a reaction inert solvent under reductive alkylation conditions.

6 Claims, No Drawings

PROCESS FOR THE PRODUCTION OF 2-SUBSTITUTED PYRIDO[4,3-B]-INDOLES

CROSS-REFERENCE TO RELATED APPLICATION

This application is a division of application Ser. No. 5,698, filed Jan. 23, 1979, which in turn is a continuation-in-part of application Ser. No. 799,392, filed May 23, 1977, and now abandoned.

BACKGROUND OF THE INVENTION

1. Field of the Invention

This invention relates to certain trans-2-substituted-5-aryl-2,3,4,4a5,9b-hexahydro-1H-pyrido[4,3-b]indole derivatives, their use as tranquilizing agents, pharmaceutical compositions thereof, a process and intermediates for their production.

2. Description of the Prior Art

Following the introduction of reserpine and chlorpromazine in psychotherapeutic medicine in the early 1950's, great effort has been expended in the search for other tranquilizing agents having improved biological profiles, several of which are γ-carboline derivatives, also known in the art as derivatives of pyrido[4,3-b]indole.

In U.S. Pat. No. 3,687,961 8-fluoro-2-[3-(4-fluorophenylanilino)propyl]-1,2,3,4-tetrahydro-γ-carboline was disclosed as a useful tranquilizer for warm-blooded animals. In U.S. Pat. No. 3,755,584 structurally related compounds with fluorine in the 6- or 8-positions and a specific p-substituted phenylalkyl moiety at the 2-position were found to have similar activity.

U.S. Pat. No. 3,983,239 disclosed hexahydro-γ-carbolines of the formula

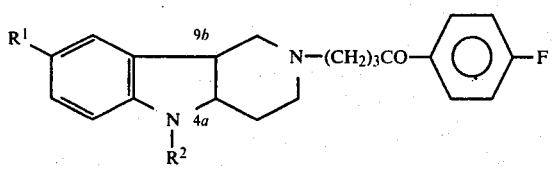

where $R^1$ is methyl or ethyl and $R^2$ is hydrogen, methyl or ethyl. The stereochemical relationship of the hydrogen atoms attached to the carbon atoms at the 4a and 9b positions is not mentioned in this reference. However, one would expect them to be in a cis relationship based on the method of formation of the hexahydro-γ-carboline nucleus from a 1,2,3,4-tetrahydro-γ-carboline precursor by catalytic hydrogenation in the presence of platinum, a method well known in the art to introduce hydrogen atoms in a cis-configuration to a carbon-carbon double bond. The compounds claimed are neuroleptic agents said to be useful in the treatment of schizophrenia.

U.S. Pat. No. 3,991,199 discloses hexahydropyrimido[4,3-b]indoles, useful as analgesics and sedatives, some of which are of interest as tranquilizers, some as mucle relaxants and many of them show hypotensive activity; the compounds disclosed are of the formula

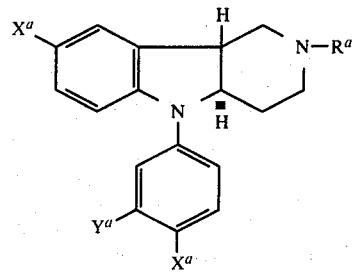

and their pharmaceutically suitable salts, where the hydrogens attached to the carbon atoms in the 4a and 9b positions are in trans relationship to each other and where: when $Y^a$ is —H, —Cl, —Br, —CH$_3$, -tert-C$_4$H$_9$ or —OCH$_3$; and when $Y^a$ is —CF$_3$, $X^a$ is —H; and $R^a$ is, inter alia, hydrogen, benzyl; benzyl ring-substituted with methyl, methoxy or chloro; phenethyl; 3-phenylpropyl; 3-phenylpropyl ring-substituted with chloro, bromo or methoxy.

Recently issued Belgian patent No. 845,368 (Derwent No. 00043Y) discloses 5-phenyl-hexahydro-β-carbolines, optionally substituted at positions 2 and 4 by methyl or ethyl and at position 3 by alkyl having from 1 to 3 carbon atoms, allyl or propargyl. They are said to be useful as antidepressants.

Recent West German Offenlegungsschrift No. 2,631,836, Derwent No. 09738Y, discloses structurally related octahydropyrido[4',3':2,3]indolo[1,7-ab][1]benzazepines which may be depicted by the above formula but with an ethylenic bridge between the two benzene rings, $Y^a$ and $X^a$ are hydrogen and $R^a$ is —CH$_2$CH$_2$COCH$_3$ or —CH$_2$CH$_2$COC$_6$H$_5$. They are said to be useful as analgesics and tranquilizing agents.

U.S. Pat. No. 4,001,263 discloses 5-aryl-1,2,3,4-tetrahydro-γ-carboline tranquilizers of the formula

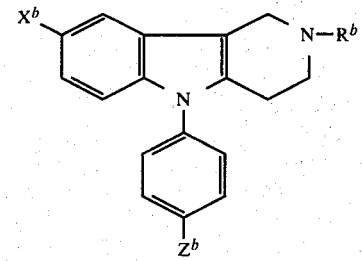

where $X^b$ and $Z_b$ may be hydrogen or fluoro and values of $R^b$ include many of the 2-substituents disclosed for the compounds of formula (I). It has now, unexpectedly, been found that the trans-2,3,4,4a,5,9b-hexahydro-1H-pyrido[4,3-b]indoles of the present invention have markedly superior tranquilizing activity when compared with the corresponding 1,2,3,4-tetrahydro-γ-carbolines.

SUMMARY

The valuable tranquilizing agents of the present invention are the 2-substituted-5-aryl-2,3,4,4a,5,9b-hexahydro-1H-pyrido[4,3-b]indoles of the formula

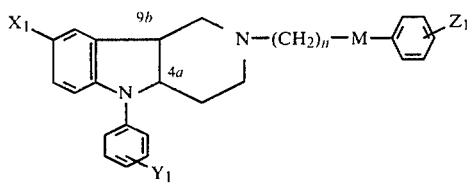

and the pharmaceutically acceptable acid addition salts thereof, wherein the hydrogens attached to the carbon atoms in the 4a and 9b positions are in a trans-relationship to each other and the 5-aryl-2,3,4,4a,5,9b-hexahydro-1H-pyrido[4,3-b]indole moiety is dextrorotatory; $X_1$ and $Y_1$ are the same or different and are each hydrogen or fluoro; $Z_1$ is hydrogen, fluoro or methoxy; M is a member selected from the group consisting of

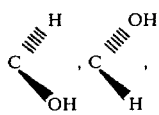

a mixture thereof and C=O and n is 3 or 4.

By the term "5-aryl-2,3,4,4a,5,9b-hexahydro-1H-pyrido[4,3-b]indole moiety" is meant the moiety of the formula A

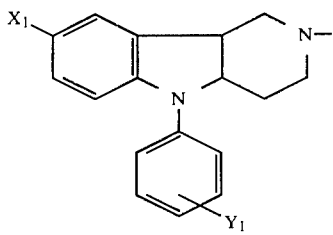

wherein the hydrogens attached to the carbon atoms in the 4a and 9b positions are in a trans-relationship to each other and $X_1$ and $Y_1$ are as defined above. The preferred compounds of the invention are those wherein said moiety (A) is dextrorotatory. The compounds of formula (I) wherein said moiety (A) is levorotatory has been found to be considerably less active as tranquilizing agents. Compounds of formula (I) having a mixture of said dextrotatory and levorotatory moieties, including the racemates, are of intermediate activity.

The invention further provides methods for the treatment of schizophrenic manifestations in mammals which comprises orally or parenterally administering to a mammal in need of such treatment a tranquilizing amount of a compound selected from those of the formula (I).

Also provided are pharmaceutical compositions active as tranquilizing agents comprising a pharmaceutically acceptable carrier and a compound selected from those of the formula (I).

The compounds of the present invention have a markedly and unexpectedly superior tranquilizing effect over the above mentioned tranquilizing agents of the prior art.

Especially preferred tranquilizing agents of the invention are the following compounds wherein the trans-5-aryl-2,3,4,4a,5,9b-hexahydro-1H-pyrido[4,3-b]indole moiety is dextrorotatory, and diastereomers thereof.

trans-8-fluoro-5-(p-fluorophenyl)-2-[4-hydroxy-4(p-fluorophenyl)butyl]-2,3,4,4a,5,9b-hexahydro-1H-pyrido[4,3-b]indole, trans-5-phenyl-2-[4-hydroxy-4-(p-methoxyphenyl)-butyl]-2,3,4,4a,5,9b-hexahydro-1H-pyrido[4,3-b]indole, trans-8-fluoro-5-(p-fluorophenyl)-2-[4-hydroxy-4-(p-methoxyphenyl)butyl]-2,3,4,4a,5,9a-hexahydro-1H-pyrido[4,3-b]indole, trans-5-phenyl-2-(4-hydroxy-4-phenylbutyl)-2,3,4,4,a,5,9b-hexahydro-1H-pyrido-[4,3-b]indole, trans-8-fluoro-5-(p-fluorophenyl)-2-(4-hydroxy-4-phenylbutyl)-2,3,4,4a,5,9b-hexahydro-1H-pyrido[4,3-b]indole, trans-5-phenyl-2-[3-(p-fluorobenzoyl)propyl]-2,3,4,4a,5,9b-hexahydro-1H-pyrido[4,3-b]indole, trans-8-fluoro-5-(p-fluorophenyl)-2-[3-(p-fluorobenzyl)-propyl-2,3,4,4a,5,9-hexahydro-1H-pyrido[4,3-b]indole, trans-8-fluoro-5-(o-fluorophenyl)-2-[4-hydroxy-4-(p-fluorophenyl)butyl]-2,3,4,4a,5,9b-hexahydro-1H-pyrido[4,3-b]indole, trans-5-phenyl-2-[4-hydroxy-4-(p-fluorophenyl)butyl]-2,3,4,4a,5,9b-hexahydro-1H-pyrido[4,3-b]indole.

Further valuable compounds of the invention, useful as intermediates are the dextrorotatory and racemic tricyclic secondary amines of the formula

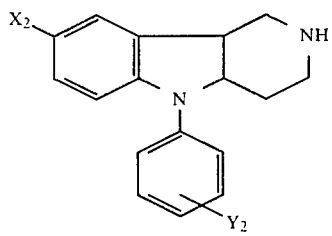

and acid addition salts thereof wherein the hydrogens attached to the carbon atoms in the 4a and 9b positions are in a trans-relationship to each other and one of $X_2$ and $Y_2$ is fluoro and the other is hydrogen or fluoro.

Also disclosed is a novel process for producing compounds of formula (I) by reductive alkylation of a tricyclic secondary amine of the formula (VIII) or (XV) with a lactol of the formula

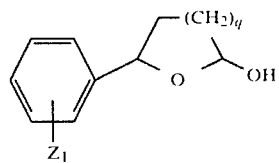

wherein $Z_1$ is as defined above and q is 1 or 2.

Other novel and valuable compounds of the invention are the enantiomeric and racemic 5-aryl-2-hydroxytetrahydrofurans of the formula

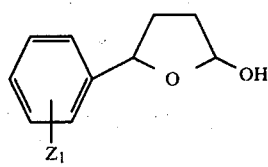

where $Z_1$ is as defined above.

DETAILED DESCRIPTION OF THE INVENTION

The tranquilizing agents of the invention are of the formula

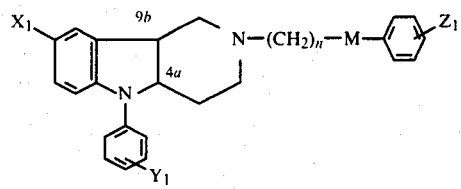

(I)

wherein the hydrogens attached to the 4a and 9b-carbon atoms are in a trans-relationship, the 5-aryl-2,3,4,4a,5,9b-hexahydro-1H-pyrido[4,3-b]-indole moiety (A) is dextrorotatory and $X_1$, $Y_1$, $Z_1$ n and M are as previously defined. As will be recognized by one skilled in the art, moiety (A) contains two assymetric carbon atoms at the 4a and 4b positions and two resolved trans forms (d- and l-) and a racemic form is possible for each value assigned to $X_1$ and $Y_1$. The moiety (A), of course does not exist alone, but may be derived, for example, from the free base of formula (A-H)

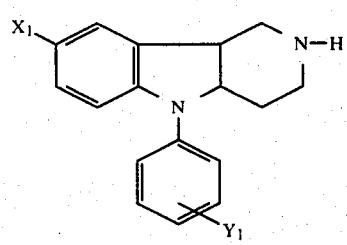

(A-H)

from which the compounds of formula (I) may be derived. Each of the compounds (AH) exists as a dextrorotatory (d-)enantiomer, a levorotatory (l-)enantiomer and as mixtures of the two including the racemate containing equal amounts of the d- and l-enantiomers. The dextrorotatory and levorotatory isomers can be distinguished by their ability to rotate the plane of plane-polarized light. The d-form is that which rotates the plane of plane-polarized light to the right and the l-form is that which rotates the plane-polarized light to the left. A racemic mixture, containing equal members of d- and l-enantiomers, does not effect the plane of plane-polarized light. For the purposes of the present invention, when determining whether a compound is dextrorotatory or levorotatory, it is the effect of the compound on light having a wavelength of 5893 Angstroms (the so-called D line of sodium) which is to be considered. A moiety of formula (A), above, is considered to be dextrorotatory if the hydrochloride salt of the free base of formula (AH) rotates such light to the right.

The following reaction scheme is illustrative of the processes which may be employed for synthesis of the 4a,9b-trans-2,3,4,4a,5,9b-hexahydro-1H-pyrido[4,3-b]indoles of formula (VIII) wherein $X_1$ and $Y_1$ are as previously defined:

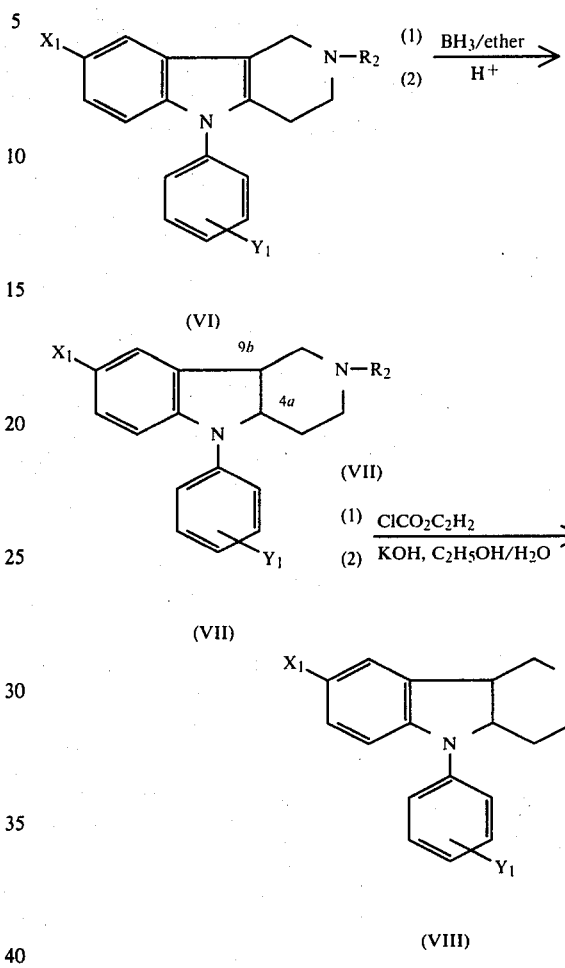

A preferred value for $R_2$ is benzyl for reasons of economy. However, other values of $R_2$ which will also serve in the above scheme will be obvious to those skilled in the art. Examples of such alternate values for $R_2$ are benzyl moieties substituted in the benzene ring by, for example, one or more members selected from the group consisting of methyl, methoxy, nitro and phenyl; and benzhydryl.

The reduction of the tetrahydro-γ-carbolines of formula (VI) to form the 4a,9b-trans-hexahydro compounds of formula (VII) is carried out in an ether solvent, usually tetrahydrofuran. In order to assure complex reduction a molar excess of borane/tetrahydrofuran complex($BH_3$·THF) is ordinarily employed and a 100 to 200% molar excess of said complex is preferred. While the reaction may be carried out at a temperature in the range of about $-10°$ to $80°$ C., a temperature of from about $0°$ to $65°$ C. is preferred. Ordinarily, a solution of the starting material of formula (VI) in tetrahydrofuran is added to an ice-cooled solution of $BH_3$·THF. After the addition is complete the reaction mixture is heated to reflux and maintained at this temperature for a period of about one to two hours or more. The reaction is ordinarily carried out in the presence of an inert gas such as nitrogen. When the reaction is substantially completed, the solvent is evaporated and the residue is acidified with an excess of an acid such as, for example, 2 to 12 molar hydrochloric acid. A preferred acidulant is a mixture of equal volumes of acetic acid and 5 molar hydrochloric acid. The acidified mixture is ordinarily heated at reflux for 1 to 2 hours or more. The desired product may then be isolated, for example, by evaporation of any residual ether solvent and a portion of the acid mixture and the precipitated product collected by filtration and washed. In an alternate method of isolation of the product (VII), after the reflux period the reaction mixture is filtered, the filtrate cooled and made alkaline by addition of, for example, sodium hydroxide, potassium hydroxide or sodium carbonate. The basic mixture is extracted with a water immiscible organic solvent such as, for example, chloroform, methylene chloride or benzene, the extracts evaporated and the residue purified by silica gel column chromatography, eluting, for example, with ethyl acetate or mixtures of hexane/ethyl acetate.

The reduction of tetrahydro-γ-carbolines by BH$_3$·THF followed by acid treatment yields hexahydro-γ-carbolines in which the hydrogens attached to the carbon atoms in the 4a and 9b positions are in a trans-relationship, see, for example, U.S. Pat. No. 3,911,199.

The 2-benzyl compounds of formula (VII) are then converted to the corresponding 2-hydrogen compounds of formula (VIII). In general, this may be accomplished by treating the compound of formula (VII) with a molar excess of a lower alkyl chloroformate ester such as, for example, the methyl, ethyl, propyl or isobutyl ester in the presence of a suitable reaction-inert organic solvent, followed by alkaline hydrolysis. Preferred as chloroformate ester is ethyl chloroformate because of its ease of availability and efficiency. By a suitable reaction-inert organic solvent is meant one which will substantially dissolve the reactants under the conditions of the reaction without the formation of byproducts. Examples of such solvents are aromatic hydrocarbons such as benzene, toluene and xylene; chlorinated hydrocarbons such as chloroform and 1,2-dichloroethane, diethyleneglycol dimethylether and dimethylsulfoxide. An especially preferred solvent is toluene.

To the mixture of starting material of formula (VII) in said reaction inert organic solvent is added up to about a ten molar excess of the chloroformate ester. For reasons of economy a molar excess of about 3 to 5 is preferable. The resulting mixture is then heated at a temperature of from about 80°–150° C., typically at the reflux temperature of the mixture, for periods of about 6 to 24 hours or more. Ordinarily, refluxing is carried out overnight for reasons of convenience. The reaction mixture is then evaporated in vacuo and the residue taken up in an alcohol-water mixture, an alkali, for example, sodium hydroxide or potassium hydroxide, is added in about 10–30 molar excess based on the amount of starting material of formula (VII), and the resulting mixture heated at reflux, typically overnight. The solvent is then evaporated and the residue partitioned between water and a water immiscible organic solvent such as, for example, chloroform, methylene chloride or ethyl ether and the organic phase evaporated to dryness. The residual product of formula (VIII) may be used as is or further purified by standard methods known in the art, for example, by column chromatography on silica gel.

In the case of compounds of the formula (VII) wherein both X and Y are hydrogen and R$_2$ is benzyl, the corresponding compound of formula (VIII) may be obtained by catalytic debenzylation employing hydrogen and palladium-on-carbon catalyst. The reaction is typically carried out employing the hydrochloride salt of the compound (VII) at a temperature of from about 50° to 100° C., preferably 60°–75° C., and hydrogen pressures of about 20–100 p.s.i. (1.4–7 kg/cm$^2$) in the presence of a reaction-inert solvent, for example, methanol, ethanol, isopropanol, ethyl acetate or mixtures thereof with water. When the hydrogen uptake is complete, the catalyst is removed by filtration and the hydrochloride salt of the product of formula (VIII) is precipitated by addition of a nonsolvent, for example, ethyl ether, benzene or hexane. Alternatively, the free base of formula (VIII) may be isolated by evaporating the filtrate from the debenzylation to dryness, partitioning the residue between aqueous alkali, for example sodium hydroxide, and a solvent such as chloroform or ethyl ether. The free base is then isolated by standard methods such as those described above.

The free bases of formula (VIII) may also serve as precursors for the novel compounds of formula (II) as illustrated by the following reacton sequence wherein X$_1$, Y$_1$, Z$_1$ and n are as previously defined.

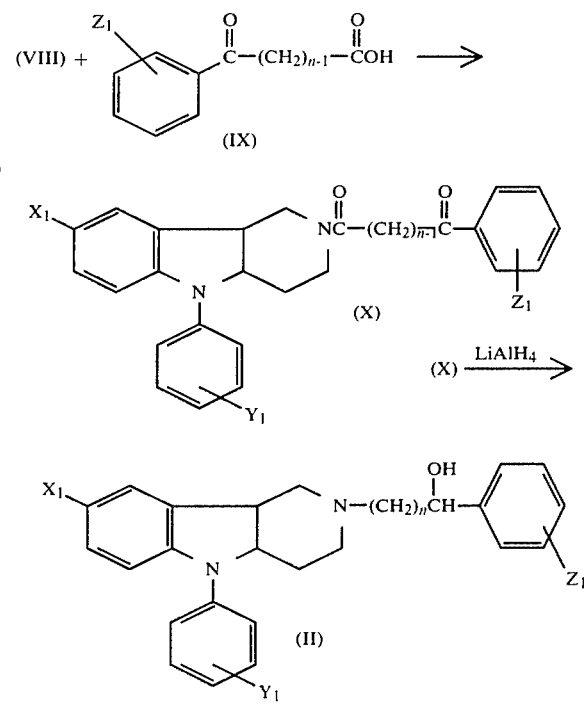

The acylation of the compounds (VIII) to form the intermediates of formula (X) may employ the acids of formula (IX) or the corresponding acid chlorides or acid bromides. When the acids of formula (IX) are employed in the acylation, approximately equimolar amounts of said acid and compound of formula (VIII) are contacted in the presence of a reaction-inert organic solvent and certain condensing agents known in the art for forming peptide bonds. Such agents include carbodiimides, for example, dicyclohexylcarbodiimide and 1-ethyl-3-(3-dimethylaminopropyl) carbodiimide hydrochloride, and alkoxyacetylenes, for example, methoxyacetylene and ethoxyacetylene. The preferred condensing agent is dicyclohexylcarbodiimide. Examples of said solvents which may be employed are dichloromethane, chloroform, tetrahydrofuran, ethyl ether and benzene. While the reaction may be carried out at a temperature of from about −10° to 50° C. with satisfactory results, it is preferred to employ a temperature of from about 0° to 30° C. At this temperature the reaction is ordinarily complete in a few hours. The product of formula (X) is isolated, for example, by filtering to remove insoluble material and evaporation of solvent. The resulting product is ordinarily of sufficient purity for use in the next step.

The intermediate of formula (X) is then reduced with lithium aluminum hydride to obtain the desired compound of formula (II). The reduction is preferably carried out in the presence of an inert gas such as nitrogen or argon and under substantially anhydrous conditions. From about 2 to 10 molar excess of lithium aluminum hydride is suspended in an ethereal solvent, for example, ethyl ether or tetrahydrofuran and the mixture is preferably cooled to a temperature of about 0° to 10° C. The intermediate of formula (X), obtained as described above, is ordinarily dissolved in the same solvent and the solution added dropwise. The resulting mixture is then reacted, ordinarily at or about room temperature for a period of from about 0.5 to 4 hours to attain substantial completion of the reaction. The excess lithium aluminum hydride is then decomposed, e.g., by cautious addition of water, the resulting mixture filtered and the filtrate evaporated to dryness to provide the desired product of formula (II) which may be further purified, if desired, by standard methods known to one skilled in the art. Alternatively, the free base, (II), may be converted to a salt such as, for example, the hydrochloride addition salt by addition of anhydrous hydrogen chloride to a solution of the base in a solvent such as ethanol, ethyl ether or mixtures thereof. The precipitated salt may then be collected, e.g., by filtration. The products (II) may be further purified, if desired, for example, by column chromatography on silica gel.

An alternate method for providing the 4a,9b-trans-compounds of formula (II) in admixture with the corresponding dehydrated compounds of formula (III) is illustrated as follows:

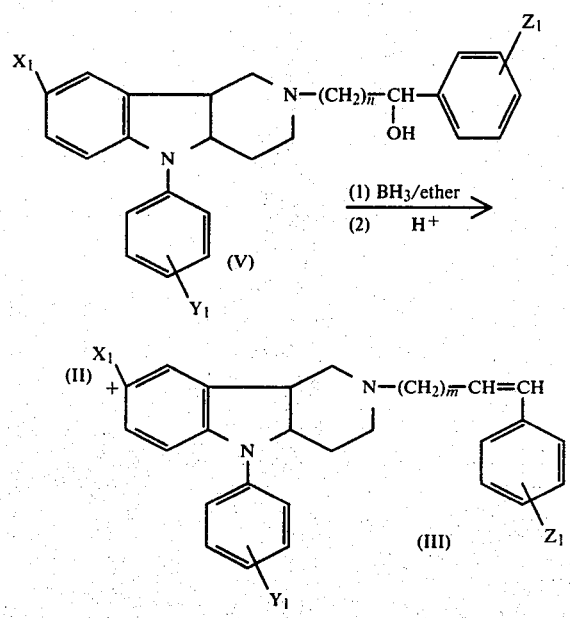

In which $X_1$, $Y_1$, $Z_1$ and n are as previously defined and m is 2 or 3. The reaction with borane in ether solvent, preferably in tetrahydrofuran, and subsequent treatment with acid, is carried out under the conditions described above for preparation of the 2-benzyl compounds of formula (VII). The products (II) and (III) are separated, for example by column chromatography on silica gel.

The relative amounts of products (II) and (III) will vary depending upon the amount of acid, for example, hydrochloric acid, and the time of heating at reflux after the reduction with $BH_3 \cdot THF$ has taken place. Higher amounts of acid and longer reflux times favor the dehydrated product of formula (III); while lower amounts of acid and shorter reflux periods favor the formation of the product (II).

The compounds of formula (II) or (III) may also serve as precursors of the free bases of formula (VIII). This is carried out employing, for example, ethyl chloroformate followed by alkaline hydrolysis as described above for the debenzylation of the compounds of formula (VII) wherein $R_2$ is benzyl, to obtain the free bases of formula (VIII).

Oxidation of the compounds of formula (II) employing reagents and conditions which are known to selectively convert secondary alcohols to the corresponding ketones, provides the novel products of formula

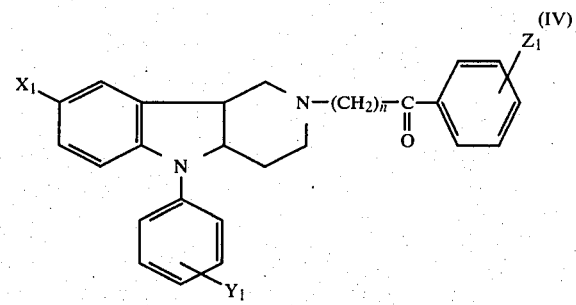

wherein $X_1$, $Y_1$, $Z_1$ and n are as previously defined. Examples of such oxidizing agents which may be employed in this reaction are potassium permanganate, potassium dichromate and chromium trioxide and the preferred reagent is chromium trioxide in the presence of pyridine. In carrying out this reaction with the preferred reagent, the starting alcohol of formula (VI) in a reaction-inert solvent, for example, dichloromethane, chloroform or benzene, is added to a mixture containing up to a ten molar excess of chromium trioxide and a similarly large molar excess of pyridine and the mixture stirred, ordinarily at room temperature, until the reaction is substantially complete. Ordinarily, from about 15 minutes to one hour will suffice. The product is isolated, for example, by removal of insoluble material by filtration, extracting the filtrate with a dilute aqueous alkali such as sodium hydroxide solution, drying the organic layer and evaporating to dryness. The residual product may be further purified, if desired, for example, by column chromatography.

As will be recognized by one skilled in the art, the 4a,9b-trans-compounds of formula (IV) and (VIII) form a single racemate which can be resolved into a pair of enantiomers, one of which is dextrorotatory and the other is levorotatory. The 4a,9b-trans-compounds of formula (II), having an additional assymmetric carbon atom in the 2-substituent, form two diastereomers, each of which is resolvable into dextrorotatory and levorotatory enantiomers.

It has now been found that the tranquilizing activity of the compounds of formula (I), resides in such compounds wherein the 5-aryl-2,3,4,4a,5,9b-hexahydro-1H- pyrido[4,3-b]indole moiety (A) is dextrorotatory. The corresponding compounds wherein moiety (A) is levorotatory being of significantly lower activity. Active tranquilizing agents included within the scope of the invention, therefore, include the enantiomers of formula (I) wherein said moiety (A) is dextrorotatory as well as mixtures of enantiomers of formula (I) wherein said moiety (A) is dextrorotatory and levorotatory, including the racemic mixtures. While the nature of the 2-substituent attached to the moiety (A) to form the compounds of formula (I) is critical for optimal tranquilizing activity, the stereochemistry of the 2-substituent is less important. Thus, compounds of formula (II) wherein moiety (A) is dextrorotatory are highly active when a given 2-substituent of formula $(CH_2)nCHOHC_6H_5Z_1$ is racemic, dextrorotatory or levorotatory and all of these are included within the scope of the invention.

The compounds of formula (II) as ordinarily obtained by the above-described methods are a mixture of diastereomers. Methods for the separation of such mixed diastereomers include fractional crystallization and chromatographic methods. The separation of mixed diastereomers of formula (II) by fractional crystallization is ordinarily sufficient to afford each of the diastereomers in a highly purified form. Of course, column chromatography may be employed to further purify the diastereomers. Solvent systems useful for the fractional crystallization of the above diastereomers include, for example, mixed solvent systems containing both a polar and non-polar solvent. Examples of such polar solvents include ethyl acetate, methanol, ethanol, acetone and acetonitrile. Examples of such non-polar solvents are hexane and its close homologs, benzene, toluene and carbon tetrachloride. A preferred mixture of such solvents is ethyl acetate and hexane.

The resolution of the single diastereomers of formula (I) into the d- and l-enantiomers can be brought about by a variety of methods known in the art for resolving racemic amines, see e.g., Fieser et. al., "Reagents for Organic Synthesis", Wiley & Sons, Inc., New York, (1967), Vol. I, p. 977 and references cited therein. However, a particularly useful method for obtaining the enantiomers from the racemates of formula (I) is by esterification of a compound of formula (II) with an optically active acid followed by separation of the diastereomeric esters by fractional crystallization or by chromatography. The enantiomeric ketones of formula (IV) are then obtained by oxidation of the corresponding enantiomers of formula (II). While a variety of optically active acids are known in the art for such use, L-phenylalanine has been found to be especially useful for resolving the diastereomers of formula (II) according to the following scheme in which (A) represents the 5-aryl-2,3,4,4a,5,9b-hexahydro-1H-pyrido[4,3-b]indole moiety and t-Boc is t-butyl-oxycarbonyl.

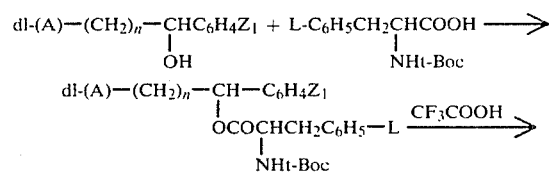

(XVI) mixture of diastereomers

-continued

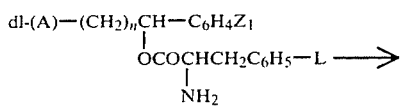

(XVII mixture of diastereomers)

(XVII, single diastereomer)

↓ H₂O (II, single enantiomer)

↓ oxidation (IV, single enantiomer)

In the first step of the resolution scheme depicted above, the single racemic diastereomer of formula (II) is esterified with t-Boc-L-phenylalanine by methods known in the art for esterification of such compounds. In a particularly preferred procedure, the diastereomer (II) is contacted with at least an equimolar amount of t-Boc-L-phenylalanine in the presence of a reaction inert solvent and a condensing agent at low temperature, preferably at about 0° to room temperature. Examples of suitable reaction inert solvents include chloroform, methylene chloride, 1,2-dichloroethane, tetrahydrofuran and ethyl ether. Preferred as solvent is chloroform and a preferred condensing agent is dicyclohexylcarbodiimide. The reaction is ordinarily complete within a few hours. The resulting ester of formula (XVI) is recovered by well known methods and reacted in the cold, preferably at −10° to 20° C. with a molar excess of trifluoroacetic acid to remove the t-butyloxycarbonyl protecting group to provide the amino ester of formula (XVII) as a mixture of diastereomers. This mixture is then separated by fractional crystallization or chromatography to provide the single diastereomers of formula (XVII). A particularly convenient method for such separation is by column chromatography on silica gel. The isolated single diastereomers are then hydrolyzed in the presence of acid or base by well known methods to provide the separated dextrorotatory and levorotatory enantiomers of formula (II). The latter enantiomers may then be oxidized, for example, by means of chromic acid as described herein, to provide the corresponding enantiomers of formula (IV).

An alternate method for providing the enantiomeric compounds of formula (II) is by stereospecific synthesis in which the resolved enantiomers of a tricyclic secondary amine of formula (VIII) are condensed with an enantiomeric precursor of the 2-position substituent. In order to effect stereospecific synthesis of the compounds of formula (II), a novel process which conveniently achieves this goal to provide optically pure compounds in high yield employing resolved reactants is outlined below. Of course, this process is also useful for providing racemic products when racemic reactants are employed.

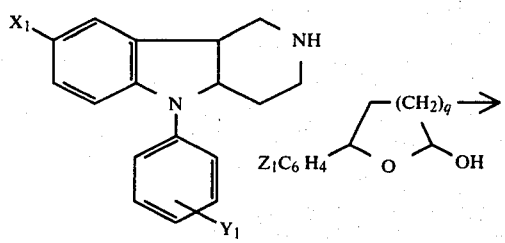

(VIII)     (XVI)

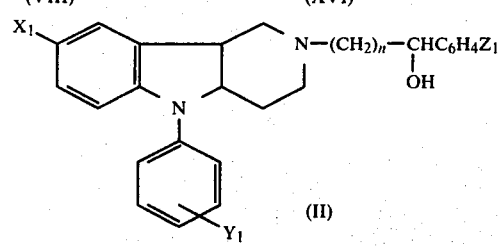

(II)

In the above reaction scheme, $X_1$, $Y_1$, $Z_1$ and n are as previously defined and q is 1 or 2.

The optical isomers of amine (VIII) are obtained by resolution of the racemic compounds. The resolution is carried out by means of a salt formed between the amine (VIII) and optically active acid. While a variety of acids useful in the resolution of amines are known in the art, see for example, Fieser et. al. cited above, preferred acids which afford ready separation of the amine (VIII) are the optical isomers (D- and L-) of N-carbamoyl-phenylalanine. The latter are obtained by reaction of the isomeric phenylalanines with sodium cyanate by methods known to one skilled in the art. The resolution is achieved by reacting one of the isomeric N-carbamoyl-phenylalanines, for example the L-isomer, with a racemic compound of formula (VIII) in equimolar amounts in the presence of a suitable reaction inert solvent to form a homogeneous solution of the salts. Upon cooling, the salt of one of the optical isomers of (VIII) is obtained as a crystalline solid which may be further purified if desired. The mother liquors containing primarily the salt of the other isomer is evaporated to dryness and the salt decomposed by aqueous base such as, for example, sodium carbonate, potassium hydroxide or calcium carbonate and the free base extracted by means of a water immiscible solvent, typically ethyl acetate, dried and the solvent evaporated to obtain a residue enriched in the second isomer of the amine (VIII). This residue is then taken up in a reaction inert solvent and treated with an equimolar amount of the other isomer of N-carbamoylphenylalanine, for example, the D-isomer and the solution cooled to precipitate crystals of the N-carbamoylphenylalanine salt of the second isomer of formula (VIII).

Each of the salts containing a single enantiomer of the amine (VIII) is then decomposed as described above to obtain, respectively, the essentially pure dextrorotatory and levorotatory isomers of (VIII).

Some of the racemic lactols of formula (XIV) wherein q is 2, are known in the art, Colonge et. al., Bull. Soc. Chem. France, 2005 (1966); Chem. Abstr., 65, 18547d (1966). However, the five-membered lactols (XIV), q=1) are novel compounds. The lactols may be prepared by various routes, for example, from the known compounds of the formula (XI) or the corresponding nitriles as shown below, wherein $Z_1$ and q are as defined above.

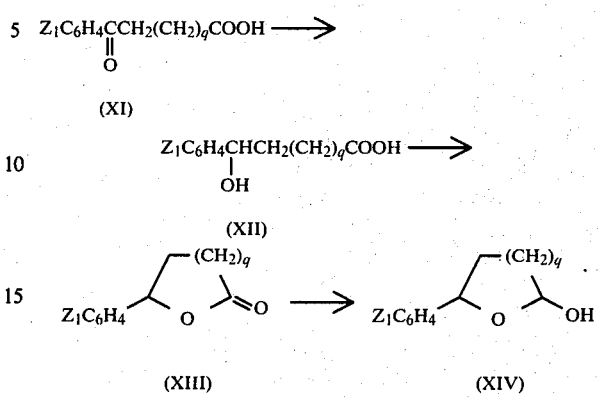

The ketoacid of formula (XI) is reduced conveniently, e.g., by means of sodium borohydride by methods known to those skilled in the art to provide the corresponding hydroxy acids of formula (XII) (or the corresponding nitrile if cyanoketones corresponding to (XI) are employed, followed by hydrolysis of the hydroxynitrile to provide the hydroxy acid). The hydroxy acids are readily converted to lactones (XIII) by warming under dehydrating conditions, preferably in the presence of a reaction inert solvent, typically ethyl acetate, and in the presence of a catalytic amount of acid, typically p-toluenesulfonic acid. The reaction mixture is ordinarily heated at reflux for about one hour, cooled, washed with brine, dried and the lactone (XIII) isolated by evaporation of solvent.

The lactone (XIII) is reduced by means of a metal hydride reducing agent to provide the lactol of formula (XIV). While a variety of metal hydride reducing agents may be employed with some success to provide the desired lactols, preferred reducing agents are diisobutyl-aluminum hydride, sodium borohydride, lithium borohydride and the former is especially preferred. The reaction is carried out in the presence of a reaction inert organic solvent and a reaction inert gas such as argon or nitrogen. When the preferred diisobutylaluminum hydride is employed as reducing agent, the reaction is carried out at a temperature of from about $-80°$ to $-70°$ C. Approximately equimolar amounts of the two reactants are employed. The reaction is ordinarily complete in a few hours or less. The reaction mixture is quenched by addition of a lower alkanol, e.g., methanol, warmed to a temperature near room temperature and the solvent evaporated in vacuo and the lactol isolated by standard methods which will be known to those skilled in the art.

As mentioned above, when enantiomeric compounds of formula (II) are desired by the reaction of amine (VIII) and lactol (XIV), resolved reactants are required. In order to obtain resolved isomers of (XIV), the resolution of the corresponding racemic hydroxyacid precursors of formula (XII) is carried out.

The resolution of racemic hydroxyacids (XII) is carried out in a manner analogous to that described above for the resolution of amines (VIII), e.g., by fractional crystallization of the salts employing first e.g., d-ephedrine to precipitate one isomer of (XII); the other isomer of (XII) is then precipitated with the antipode of ephedrine and the two salts decomposed to obtain the dextrorotatory and levorotatory isomers of (XII), each of which is converted to lactol (XIV) as described above. For the synthesis of each of the enantiomers of formula (II) equimolar amounts of the resolved reactants of formula (VIII) and (XIV) are contacted in the presence of a reaction inert organic solvent under reductive alkylation conditions. Methods for carrying out reductive alkylation reactions have been reviewed, for example, by Emerson, *Organic Reactions* 4, 174 (1948) and by Rylander in "Catalytic Hydrogenation Over Platinum Metals", Academic Press, New York, 1967, p. 291–303. The the reaction may be effected with a wide variety of reducing agents known to be useful for reductive alkylation of secondary amines with aldehydes and ketones such as, for example, hydrogen in the presence of a catalytic amount of a noble metal catalyst such as platinum, palladium, rhodium, ruthenium or nickel; various metal hydride reducing agents such as sodium cyanoborohydride, sodium borohydride and lithium borohydride; and formic acid. Preferred reducing agents are (1) sodium cyanoborohydride or (2) hydrogen in the presence of noble metal catalysts. Especially preferred noble metals are platinum and palladium and most particularly preferred is palladium for reasons of economy and efficiency in providing enantiomeric products in high yield and with a high degree of optical purity.

In its preferred embodiment the amine of formula (VIII) is contacted with an equimolar amount of lactol of formula (XIV) and one of the above-mentioned preferred reducing agents in the presence of reaction inert organic solvent at a temperature of from about $-10°$ to $50°$ C. When the preferred reducing agent is sodium cyanoborohydride, at least an equivalent amount is employed. When the preferred noble metal catalysts are employed, the reaction is carried out in the presence of a molar excess of hydrogen.

As mentioned above, the noble metal catalyst is employed in a "catalytic amount", which term is well understood by those skilled in the art. When the noble metal catalysts and hydrogen are employed, the reaction may be carried out at atmospheric pressure or at high pressures up to about 10 atmospheres or higher with equal facility. The factor which will ordinarily determine whether the reaction is carried out at atmospheric pressure or higher pressure is the scale on which reaction is carried out. For example, when carried out on a few grams or less of reactants, atmospheric pressure is more convenient; however, on a commercial scale, use of high pressure is usually preferable.

Examples of suitable reaction inert solvents are the lower alkanols, such as methanol, ethanol, isopropanol and n butanol, ethers such as dimethoxyethane, diethyleneglycol dimethyl ether, ethyl ether and isopropyl ether, glycols such as ethylene glycol and ethylene glycol, and glycol monoethers such as α-methoxyethanol and diethyleneglycol monomethyl ether.

While the reaction may be carried out with some success at temperatures of from about $-50°$ up to the reflux temperature of the solvent, preferred reaction temperature is from about $-10°$ to $50°$ C. for reasons of convenience and efficiency. At higher temperatures, racemization of products and other undesired side reactions may take place to an appreciable extent. At temperatures lower than $-10°$ C., the reaction rate is very slow. The reaction ordinarily proceeds to completion in from about one to five hours. The products are then isolated by standard methods and purified, if desired, for example, by crystallization or chromatography. The desired enantiomeric products are thus obtained in good yield and are of high optical purity.

An alternative preferred product of the invention is obtained by the above procedure using dextrorotatory amine (VIII) and racemic lactol (XIV) in the above procedure. The product obtained, of formula (II), is optically active due to the chirality of the amine moiety (A), defined above. It is a highly active tranquilizing agent and also serves as an economical intermediate for oxidation by methods described above, to the ketonic products of formula (IV).

2-Benzyl-5-phenyl-1,2,3,4-tetrahydro-2-carboline is obtained by the Fischer indole synthesis employing N,N-diphenylhydrazine and N-benzyl-4-piperidone. The mono or difluoro-substituted starting tetrahydro-γ-carbolines of formula (VI) wherein at least one of $X_1$ or $Y_1$ is fluoro and $R_2$ is benzyl, are prepared from the corresponding compounds of formula (VI) wherein $R_2$ is hydrogen by reaction with a benzyl halide such as benzyl bromide, in equimolar amounts. The requisite compounds of formula (VI, $R_2=H$) are prepared as described in U.S. Pat. No. 4,001,263. The starting tetrahydro-γ-carbolines (V) are described in the same reference.

Except for the novel intermediates of formulae (VIII) and (XIV) mentioned above, the other starting materials are either commercially available, their preparation is explicitly reported in the chemical literature or they can be prepared by methods known to those skilled in the art. For example, the phenylhydrazines are commercially available or are synthesized by reduction of the phenyldiazonium salt as reviewed by Wagner and Zook in "Synthetic Organic Chemistry", John Wiley & Sons, New York, N.Y., 1956, Chapter 26; the 1-substituted-4-piperidones are commercial reagents or prepared by the method of McElvain et al., *J. Am. Chem. Soc.*, 70, 1826(1948); the requisite 3-benzoylpropionic acids and 4-benzoylbutyric acids are either commerically available or prepared by modification of the procedure of "Organic Synthesis", Coll. Vol. 2, John Wiley & Sons, New York, N.Y., 1943, p. 81.

As has been previously mentioned, the basic compounds of the present invention can form acid addition salts. Said basic compounds are converted to their acid addition salts by interaction of the base with an acid either in an aqueous or nonaqueous medium. In a similar manner, treatment of the acid addition salts with an equivalent amount of an aqueous base solution, e.g., alkali metal hydroxides, alkali metal carbonates and alkali metal bicarbonates or with an equivalent amount of a metal cation which forms an insoluble precipitate with the acid anion, results in the regeneration of the free base form. The bases thus regenerated may be reconverted to the same or a different acid addition salt.

In the utilization of the chemotherapeutic activity of said salts of the compounds of the present invention, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutical acceptable bases by decomposition of the salt as described above, or alternately, they can be converted to any desired pharmaceutically acceptable acid addition salt.

Examples of acids which provide pharmaceutically acceptable anions are hydrochloric, hydrobromic, hydroiodic, nitric, sulfuric, sulfurous, phosphoric, acetic, lactic, citric, tartaric, succinic, maleic and gluconic acids.

As previously indicated, the compounds of the present invention are readily adapted to therapeutic use a tranquilizing agents in mammals.

The tranquilizing agents of the present invention are characterized by relief of such schizophrenic manifestations in humans as hallucinations, hostility, suspiciousness, emotional or social withdrawal, anxiety, agitation and tension. A standard procedure of detecting and comparing tranquilizing activity of compounds in this series and for which there is an excellent correlation with human efficacy is the antagonism of amphetamine-induced symptoms in rat tests, as taught by A. Weissman, et al., *J. Pharmacol. Exp. Ther.*, 151, 339 (1966) and by Quinton, et al., *Nature,* 200, 178, (1963).

Another method recently reported by Leyson et al., *Biochem. Pharmacol.*, 27, 307–316 (1978), the inhibition of $^3$H-spiroperidol binding to dopamine receptors, correlates with the relative pharmacological potencies of drugs in affecting behavior mediated by dopamine receptors.

The γ-carbolines and the pharmaceutically acceptable salts thereof, which are useful as tranquilizers, can be administered either as individual therapeutic agents or as mixtures of therapeutic agents. They may be administered alone, but are generally administered with a pharmaceutical carrier selected on the basis of the chosen route of administration and standard pharmaceutical practice. For example, they can be administered orally in the form of tablets or capsules containing such excipients as starch, milk sugar, or certain types of clay, etc. They can be administered in the form of elixirs or oral suspensions with the active ingredients combined with emulsifying and/or suspending agents. They may be injected parenterally, and for this use they, or appropriate derivatives, may be prepared in the form of sterile aqueous solutions. Such aqueous solutions should be suitably buffered, if necessary, and should contain other solutes such as saline or glucose to render them isotonic.

Although the use of the present invention is directed toward the treatment of mammals in general, the preferred subject is humans. Obviously, the physician will ultimately determine the dosage which will be most suitable for a particular individual, and it will vary with age, weight and response of the particular patient, as well as with the nature and extent of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same level as produced by a smaller quantity administered parenterally.

Having full regard for the foregoing factors, it is considered that a daily dosage of the compounds of the instant invention in humans of approximately 0.1 to 100 mg., with a preferred range of 0.5 to 25 mg, will tranquilize effectively. In those individually in which the compounds of the present invention have a prolonged effect, the dose can be 5 to 125 mg. a week, administered in one or two divided doses. The values are illustrative and there may, of course, be individual cases where higher or lower dose ranges are merited.

The following examles are provided solely for the purpose of illustration and are not to be construed as limitations of the invention, many variations of which are possible without departing from the spirit of scope thereof.

EXAMPLE 1 dl-trans-2-benzyl-2,3,4,4a,5,9b-hexahydro-5-phenyl-1H-pyrido-[4,3-b]indole Hydrochloride To a solution of 0.140 moles of borane in 150 ml. of tetrahydrofuran stirred at 0° C. in a three-necked round bottom flask fitted with magnetic stirrer, thermometer, condenser and addition funnel, and maintained under a nitrogen atmosphere, was added a solution of 23.9 g. (0.071 mole) of 2-benzyl-5-phenyl-1,2,3,4-tetrahydropyrido[4,3-b]indole in 460 ml. of dry tetrahydrofuran. The addition was carried out at such a rate as to maintain the reaction temperature below 9° C. When the addition was completed the resulting mixture was heated to reflux and maintained at this temperature for one hour. The solvent was then evaporated in vacuo to afford a white solid mass which was suspended in 40 ml. of dry tetrahydrofuran and heated, slowly at first, with 180 ml. of a 1:1 by volume mixture of acetic acid and 5 N hydrochloric acid. The resulting suspension was heated at reflux for one hour, then cooled. Evaporation of tetrahydrofuran and part of the acetic acid resulted in precipitation of a white solid which was separated by filtration and washed with water. The solid was resuspended in tetrahydrofuran, filtered, washed with ethyl ether and air dried to afford 16.7 g. (63%) of the desired trans-isomer. M.P. 256°–260° C.

Evaporation of the mother liquor gave an additional 7.2 g. of product.

When the above procedure is repeated, but employing the appropriately substituted 2-benzyl-5-phenyl-1,2,3,4-tetrahydropyrido[4,3-b]indole as starting material, the following 4a,9b-trans-compounds are obtained in like manner as their hydrochloride salts.

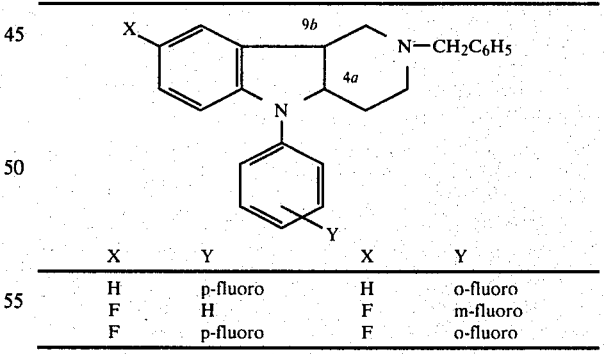

| X | Y | X | Y |
|---|---|---|---|
| H | p-fluoro | H | o-fluoro |
| F | H | F | m-fluoro |
| F | p-fluoro | F | o-fluoro |

EXAMPLE 2 dl-trans-5-Phenyl-2,3,4,4a,5,9b-hexahydro-1H-pyrido[4,3-b]indole

A suspension of 4.17 g. dl-trans-2-benzyl-5-phenyl-2,3,4,4a,5,9b-hexahydro-1H-pyrido[4,3-b]indole hydrochloride in 150 ml. of absolute ethanol was hydrogenated at 50 p.s.i. and 60°–70° C. using 1.0 g. of 10% Pd/C catalyst, over a two-hour period. The catalyst was removed by filtration and to the filtrate was added sufficient ethyl ether to precipitate the hydrochloride of the desired product, 2.76 g. (87%), M.P. 235°-237° C.

The hydrochloride salt was converted to free base by partitioning between ether and dilute sodium hydroxide solution. The ether layer was dried over sodium sulfate and evaporated to afford the title compound (97% yield), M.P. 74°-76° C.

EXAMPLE 3 di-trans-8-Fluoro-5-(p-fluorophenyl)-2-[4-hydroxy-4-(p-fluorophenyl)butyl]-2,3,4,4a,5,9b-hexahydro-1H-pyrido[4,3-b]indole hydrochloride and dl-trans-8-Fluoro-5-(p-fluorophenyl)-2-[4-(p-fluorophenyl)-3-butenyl]-2,3,4,4a,5,9b-hexahydro-1H-pyrido[4,3-b]indole hydrochloride In a 1000 ml. reaction vessel equipped with magnetic stirrer, dropping funnel and maintained under a nitrogen atmosphere were placed 177 ml. of 0.94 molar borane in tetrahydrofuran. The solution was cooled in an ice bath and to the cold solution was added over 30 minutes a solution of 25 g. (0.0555 mole) of 8-fluoro-5-(p-fluorophenyl)-2-[4-hydroxy-4-(p-fluorophenyl)-butyl]-2,3,4,5-tetrahydropyrido[4,3-b]indole in 295 ml of tetrahydrofuran. The resulting mixture was stirred at ambient temperature for 20 minutes, then heated at reflux for two hours. The reaction mixture was cooled and concentrated in vacuo to obtain a liquid residue. To this was added a mixture of 50 ml. each of acetic acid and 5 N hydrochloric acid whereupon vigorous gas evolution took place. The mixture was heated at reflux for one hour, cooled to room temperature and filtered. The filtrate was cooled in ice and made alkaline by addition of 50% (w/w) sodium hydroxide solution. The basic mixture was extracted twice with 150 ml. portions of chloroform, the combined organic layers dried over magnesium sulfate and evaporated to dryness in vacuo to obtain a yellow foamed solid, 25 g. Silica gel thin-layer chromatography, employing a 1:1 by volume hexane/ethyl acetate solvent system, revealed two products. The foamed solid was chromatographed on a column of silica gel, eluting with 1:1 by volume hexane/ethyl acetate and monitoring the fractions by TLC. The fractions containing only the faster moving product, i.e. 8-fluoro-5-(p-fluorophenyl)-2-[4-(p-fluorophenyl)-3-butenyl]-2,3,4,4a,5,9b-hexahydro-1 N-pyrido[4,3-b]indole (a mixture of diastereomers) were evaporated to dryness taken up in acetone and converted to the hydrochloride salt by addition of anhydrous hydrogen chloride in acetone, the resulting white solid was collected by filtation and dried to obtain 1.5 g. of the 3-butenyl compound, M.P. 270°-273° C.

The fractions containing only the slower moving 8-fluoro-5-(p-fluorophenyl)-2-[4-hydroxy-4-(p-fluorophenyl)butyl]-2,3,4,4a,5,9b-hexahydro-1H-pyrido[4,3-b]indole were concentrated, taken up in ethyl ether and converted to hydrochloride salt by addition of anhydrous hydrogen chloride to obtain 10.8 g. of this product, M.P. 241°-245° C., a mixture of two diastereomers.

The proportion of the faster moving 3-butenyl compound is increased, up to 100%, by suitable increase in the acidity and period of heating at reflux in the acetic/hydrochloric acid mixture.

EXAMPLE 3A

When the procedure of Example 3 was repeated, but starting with 8-fluoro-5-(o-fluorophenyl)-2-[4-hydroxy-4-(p-fluorophenyl)butyl]-2,3,4,5-tetrahydropyrido[4,3-b]indole, the faster moving component from silica gel chromatography was identified as trans-8-fluoro-5-(o-fluorophenyl)-2-[4-(p-fluorophenyl)-3-butenyl]-2,3,4,4a,5,9b-hexahydro-1H-pyrido[(4,3-b]indole, M.P. 141°-142° C. The slower moving component was identified as trans-8-fluoro-5-(o-fluorophenyl)-2-[4-hydroxy-4-(p-fluorophenyl)butyl]-2,3,4,4a,5,9b-hexahydro-1H-pyrido[4,3-b]-indole, M.P. 195°-197° C. Each of the above products was a mixture of diastereomers.

EXAMPLE 4

Employing the appropriate compounds of formula (V) as starting materials in the procedure of Example 3, the indicated 4a,9b-trans-products of formulae (II) and (III) were obtained and separated in each case. In the products of formula (III) m=n−1.

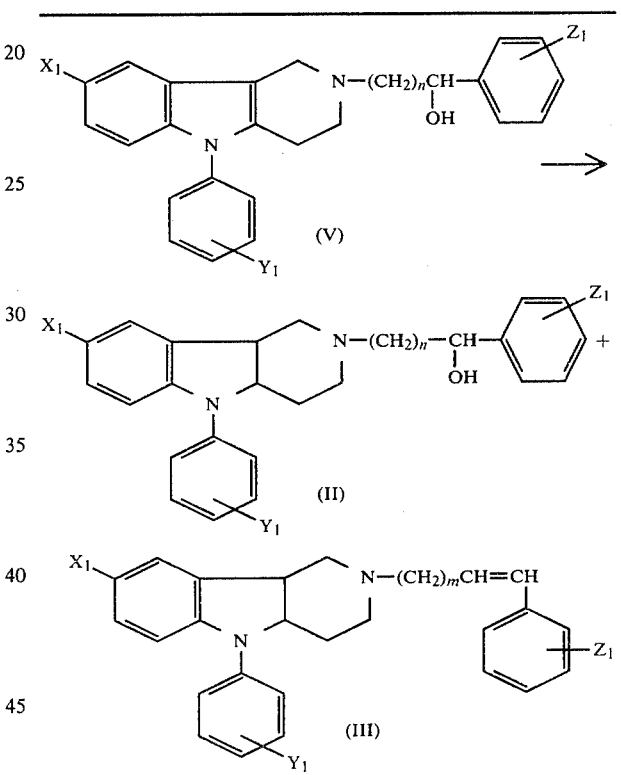

| n | X | Y | Z |
|---|---|---|---|
| 3 | F | p-fluoro | m-fluoro |
| 3 | F | p-fluoro | H |
| 3 | H | p-fluoro | p-methoxy |
| 3 | F | H | o-methoxy |
| 3 | H | H | p-fluoro |
| 4 | F | p-fluoro | p-fluoro |
| 4 | F | p-fluoro | p-methoxy |
| 4 | F | p-fluoro | H |
| 4 | F | H | o-fluoro |
| 4 | F | H | m-methoxy |
| 4 | H | p-fluoro | p-fluoro |
| 4 | H | p-fluoro | H |
| 4 | H | H | H |
| 4 | H | o-fluoro | p-fluoro |
| 3 | H | o-fluoro | p-fluoro |
| 3 | H | m-fluoro | m-fluoro |
| 3 | F | o-fluoro | p-methoxy |
| 3 | H | m-fluoro | H |
| 4 | F | o-fluoro | o-fluoro |
| 4 | F | m-fluoro | p-methoxy |

EXAMPLE 5 dl-trans-8-Fluoro-5-(p-fluorophenyl)-2,3,4,4a,5,9b-hexahydro-1H-pyrido[(4,3-b]indole A. To a solution of 5.6 g. (12.4 mmole) of dl-trans-8-fluoro-5-(p-fluorophenyl)-2-[4-hydroxy-4-(p-fluorophenyl)butyl]-2,3,4,4a,5,9b-hexahydro-1H-pyrido[4,3-b]indole in 40 ml. of toluene was added 5.3 ml. (55.7 mmole) of ethyl chloroformate. The resulting mixture refluxed overnight then evaporated to dryness to obtain a residual gum. To the gum was added 200 ml. of a 9:1 by volume mixture of ethanol/water. After the gum was dissolved, 15 g. of potassium hydroxide was added and the resulting mixture refluxed overnight. The solvent was evaporated in vacuo and the residue partitioned between water and chloroform. The organic extracts were washed with water, dried over sodium sulfate and evaporated to dryness. The residual oil was taken up in ethyl acetate and passed through a silica gel column eluting first with ethyl acetate to remove by-products then eluting the desired products with 1:1 by volume ethyl acetate/methanol. The fractions containing the title compound were combined and evaporated to dryness to obtain 1.5 g. (43%) of yellow gum which crystallized upon standing, M.P. 115°–117° C.

B. Alternately, dl-trans-2-benzyl-8-fluoro-5-(p-fluorophenyl)-2,3,4,-4a,5,9b-hexahydro-1H-pyrido[4,3-b]indole hydrochloride is refluxed in the presence of excess ethyl chloroformate or the corresponding methyl, isopropyl or n-butyl chloroformate esters, then hydrolyzed and worked up by the procedure described above to obtain the title compound.

EXAMPLE 6

Employing the appropriate starting material in each case and employing the procedures of Example 5A or 5B, the following products are similarly obtained:

dl-trans-5-(p-fluorophenyl)-2,3,4,4a,5,9b-hexahydro-1H-pyrido[4,3-b]-indole,
dl-trans-8-fluoro-5-phenyl-2,3,4,4a,5,9b-hexahydro-1H-pyrido[4,3-b]-indole,
dl-trans-5-(o-fluorophenyl)-2,3,4,4a,5,9b-hexahydro-1H-pyrido[4,3-b]-indole,
dl-trans-5-(o-fluorophenyl)-8-fluoro-2,3,4,4a,5,9b-hexahydro-1H-pyrido[4,3-b]indole,
dl-trans-5-(m-fluorophenyl)-8-fluoro-2,3,4,4a,5,9b-hexahydro-1H-pyrido[4,3-b]indole,
dl-trans-5-(m-fluorophenyl)-2,3,4,4a,5,9b-hexahydro-1H-pyrido[4,3-b]-indole.

EXAMPLE 7 dl-trans-2-(4-Hydroxy-4-phenylbutyl)-5-phenyl-2,3,4,4a,5,9b-hexahydro-1H-pyrido[4,3-b]indole Hydrochloride A. To the suspension arising from the admixture of 865 mg. (4.20 mmole) of dicyclohexylcarbodiimide and 748 mg. (4.20 mmole) of 3-benzoylpropionic acid in 30 ml. of dichloromethane at 0° C. was added 1.0 g. (4.0 mmole) of dl-trans-5-phenyl-2,3,4,4a,5,9b-hexahydro-1H-pyrido[4,3-b]indole in 10 ml. of the same solvent. The resulting mixture was stirred and allowed to warm to room temperature over 2 hours. After cooling again to 0° C. the reaction mixture was filtered, washed with dichloromethane and the filtrates evaporated to obtain a residue of dl-trans-2-[(3-benzoyl)propionyl]-5-phenyl-2,3,4,4a,5,9b-hexahydro-1H-pyrido[4,3-b]indole which was used without purification in the next step.

B. The residue from above was dissolved in 50 ml. of tetrahydrofuran and heated to reflux. A filtered solution of lithium aluminum hydride in the same solvent was added until gas evolution ceased (molar excess), and the resulting mixture was stirred at reflux for 5–10 minutes, then cooled. Anhydrous powdered sodium sulfate, 17 g., was added followed by 0.5 ml. of water. The resulting mixture was stirred at room temperature for 30 minutes, filtered, and the filtrate evaporated to dryness in vacuo. The residue was chromatographed on a column containing 80 g. of silica gel, eluting with 4:1 (v/v) ethyl acetate/methanol to afford the free base of the title compound after evaporation of solvent. The free base was converted to the hydrochloride salt by dissolving it in ether, adding a saturated solution of anhydrous hydrogen chloride in ether until precipitation was complete, filtering and drying to afford 1.04 g., M.P. 222°–224° C. Infrared spectrum (KBr), $\mu$: 2.97, 3.43, 4.00 (broad), 6.25, 6.68, 6.88, 7.51, 7.96, 8.18, 8.45, 9.82; Mass spectrum, M/e, 398, 292, 263, 249, 220, 207, 192 (100%); UV (methanol) $\lambda_{max}$245 ($\epsilon$=0.653×10$^4$), 270 ($\epsilon$=0.914×10$^4$).

EXAMPLE 8

Employing the appropriate starting material in each case selected from the free bases provided in Examples 2 and 5 and the appropriate 3-benzoylpropionic acid, the following dl-trans-compounds were prepared by the procedure of Example 9. Products were isolated as the hydrochloride salts except as indicated.

| $X_1$ | $Y_1$ | $Z_1$ | M.P., °C. | Yield, % |
|---|---|---|---|---|
| F | F | H | 220–223 | 18 |
| H | H | F | 239–245 | 39 |
| H | H | CH$_3$O | amorphous solid (a) | 54 |
| F | F | CH$_3$O | 45–48.5 (b) | 31 |

(a) Mass spectrum, M/e: 428, 411, 263 (100%), 220, 206, 204; Infrared spectrum (KBr), $\mu$: 2.98, 3.42, 4.07 (broad), 6.20, 6.26, 6.70, 6.88, 8.04, 8.54, 9.77, 12.05.
(b) Melting point and yield data are for the free base.

EXAMPLE 9

Starting with the appropriate dl-trans-hexahydro-1H-pyrido[4,3-b]-indole selected from the products of Examples 2, 5 and 6 and the appropriately substituted 3-benzoylpropionic or 4-benzoylbutyric acid, the following compounds are obtained by the method of Example 7.

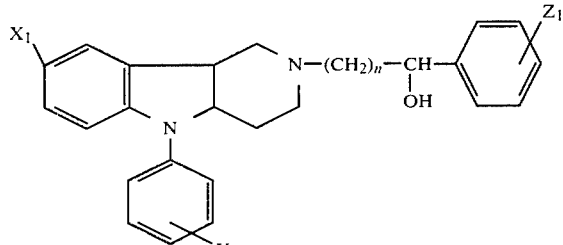

| n | $X_1$ | $Y_1$ | $Z_1$ |
|---|---|---|---|
| 3 | F | p-fluoro | m-fluoro |
| 3 | F | p-fluoro | o-methoxy |
| 3 | F | H | p-fluoro |
| 3 | H | p-fluoro | p-methoxy |
| 3 | H | o-fluoro | m-methoxy |
| 3 | F | H | H |
| 3 | H | m-fluoro | H |
| 3 | H | H | m-fluoro |
| 4 | F | p-fluoro | p-fluoro |
| 4 | F | p-fluoro | p-methoxy |
| 4 | F | o-fluoro | H |
| 4 | F | H | H |
| 4 | F | H | m-methoxy |
| 4 | H | p-fluoro | H |
| 4 | H | m-fluoro | o-fluoro |
| 4 | H | o-fluoro | p-methoxy |
| 4 | H | H | o-methoxy |
| 3 | H | p-fluoro | p-fluoro |
| 3 | H | o-fluoro | o-fluoro |
| 3 | F | m-fluoro | p-fluoro |
| 3 | H | m-fluoro | p-fluoro |

EXAMPLE 10 dl-trans-5-Phenyl-2-[3-(p-fluorobenzoyl)propyl]-3,4,4a,5,9b-hexahydro-1H-pyrido[4,3-b]indole Hydrochloride In a 25 ml. reaction vessel equipped with magnetic stirrer and maintained under a nitrogen atmosphere were placed 0.828 ml. (8.0 mg., 10.3 mmole) of dry pyridine and 10 ml. of dichloromethane. To the solution was added 517 mg. (5.17 mmole) of chromium trioxide and the resulting dark red suspension stirred for 15 minutes at room temperature. A solution of 359 mg. (0.862 mmole) of dl-trans-5-phenyl-2-[4-hydroxy-4-(p-fluorophenyl)butyl]-2,3,4,4a,5,9b-hexahydro-1H-pyrido[4,3-b]indole free base in 5 ml. of dichloromethane was added in one portion. The reaction mixture quickly changed to a brown suspension. This was stirred at ambient temperature for 30 minutes. The insoluble material was removed by filtration, washed with dichloromethane and the combined filtrate and washings were extracted with 20 ml. of 10% sodium hydroxide solution. The organic layer was dried (MgSO$_4$) and evaporated to dryness in vacuo to afford a gum. The gum was purified by column chromatography on silica gel, eluting with 1:1 by volume hexane/ethyl acetate. The fractions containing the desired product were combined, evaporated to a yellow gum, the gum taken up in ethyl ether and treated with anhydrous hydrogen chloride. The resulting suspension was evaporated to dryness, slurried with 3 ml. of cold dichloromethane. A colorless solid formed which was collected by filtration and dried to afford 20 mg. of the title compound, M.P. 244°–246.5° C.

EXAMPLE 11 dl-trans-8-Fluoro-5-(p-fluorophenyl)-2-[3-(p-fluorobenzoyl)propyl]-2,3,4,4a,5,9b-hexahydro-1H-pyrido[4,3-b]indole Hydrochloride To a 100 ml. flask containing 20 ml. of dichloromethane and 1.76 ml. (21.9 mmole) of pyridine was added 1.09 g. of chromium trioxide and the resulting dark suspension was stirred at ambient temperature for 15 minutes. Then was added in one portion a solution of 824 mg. (1.82 mmole) of dl-trans-8-fluoro-5-(p-fluorophenyl)-2-[4-hydroxy-4-(p-fluorophenyl)butyl]-2,3,4,4a,5,9b-hexahydro-1H-pyrido[4,3-b]indole free base (obtained from the hydrochloride salt by making an aqueous solution alkaline with sodium hydroxide, extracting with dichloromethane and evaporating the extracts to dryness) in 10 ml. of dichloromethane. The resulting red-brown suspension was stirred at ambient temperature for one hour and worked-up by the same procedure employed in Example 10 to obtain 25 mg. of the desired product, M.P. 260°–263° C.

EXAMPLE 12

Employing the appropriate starting material selected from the products obtained in Example 7, 8 and 9 and oxidizing by the procedure of Example 10 affords the following 4a,9b-trans compounds:

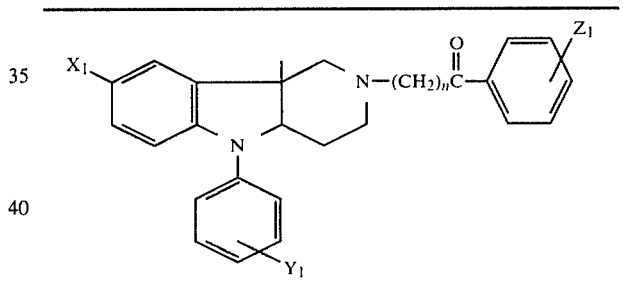

| n | $X_1$ | $Y_1$ | $Z_1$ |
|---|---|---|---|
| 3 | F | p-fluoro | H |
| 3 | H | H | p-fluoro |
| 3 | H | H | p-methoxy |
| 3 | F | p-fluoro | p-methoxy |
| 3 | H | p-fluoro | p-methoxy |
| 3 | H | o-fluoro | m-methoxy |
| 3 | F | H | p-fluoro |
| 3 | F | H | H |
| 3 | H | H | H |
| 3 | F | p-fluoro | m-fluoro |
| 3 | H | m-fluoro | H |
| 4 | F | p-fluoro | p-fluoro |
| 4 | F | p-fluoro | p-methoxy |
| 4 | F | o-fluoro | H |
| 4 | F | H | H |
| 4 | F | H | m-methoxy |
| 4 | H | p-fluoro | H |
| 4 | H | m-fluoro | o-fluoro |
| 4 | H | o-fluoro | p-methoxy |
| 4 | H | H | o-methoxy |
| 3 | H | p-fluoro | p-fluoro |
| 3 | H | o-fluoro | o-fluoro |
| 3 | F | m-fluoro | p-fluoro |
| 3 | H | m-fluoro | p-fluoro |

EXAMPLE 13

Separation of Diastereomers of dl trans-8-fluoro-5-(p-fluorophenyl)-2-[4-hydroxy-4-(p fluorophenyl)butyl]-2, 3,4,4a,5,9b-hexahydro-1H-pyrido[4,3-b]indole A. Five grams of the mixture of diastereomers of dl-trans 8-fluoro-5-(p-fluorophenyl)-2-[4-hydroxy-4-(p fluorophenyl)butyl]-2,3,4,4a,5,9b-hexahydro-1H-pyrido[4,3-b]indole hydrochloride provided in Example 3 was converted to the free base by partitioning between methylene chloride and 10% aqueous sodium hydroxide. The organic phase was dried ($Na_2SO_4$) and evaporated to a foam which was dissolved in 12.5 ml. of ethyl acetate and 45 ml. of hexane at the boiling point of the mixture. After cooling over night, the precipitated product was collected by filtration to obtain 2.24 g. of product, M.P. 126°–129° C. This was recrystallized three times from ethyl acetate/hexane to give 1.22 g. of one diastereomer, designated as the $\alpha\beta$-diastereomer, M.P. 132°–134° C. This free base was converted to the hydrochloride salt by addition of an ethereal hydrogen chloride solution to a solution of the free base in methanol to obtain 1.30 g., M.P. 259°–260° C. High pressure liquid chromatography analysis indicated that it was $\geq 99\%$ pure $\alpha\beta$-diastereomer.

B. The mother liquor from the first crystallization, above, was evaporated to a gum, dissolved in ethyl ether and converted to hydrochloride salt by addition of ethereal hydrogen chloride solution. The resulting crystalline solid was recrystallized three times from a mixture of acetonitrile/methanol, ultimately affording 1.03 g. of the second diastereomer, designated as the $\gamma\delta$-diastereomer, M.P. 237°–239° C.

High pressure liquid chromatography analysis of this produce showed that it was about 95%, by weight, pure $\gamma\delta$-diastereomer contaminated with about 5% of the $\alpha\beta$-diastereomer.

EXAMPLE 14

Resolutions of diastereomers of dl-trans-8-fluoro-5-(p-fluorophenyl)2-(4-hydroxy-4-(p-fluorophenyl)butyl]-2,3,4,4a,5,9b-hexahydro-1H-pyrido[4,3-b]indole.

A. Resolution of $\alpha\beta$-diastereomer into $\delta$-Enantiomer and $\beta$-Enantiomer.

A solution of 2.40 g. (5.3 mmole) of racemic $\alpha\beta$-diastereomer, obtained above, and 2.0 g. (7.5 mmole) of N-t butoxycarbonyl-L phenylalanine in 80 ml. of chloroform was cooled in the ice-bath under a nitrogen atmosphere. To the stirred solution was added 1.55 g. (7.5 mmole) of dicyclohexylcarbodiimide and the resulting mixture was stirred for one hour at 0° C. and another hour at room temperature. The precipitated solid (urea) was separated by filtration and washed with methylene chloride. The filtrate and washings were evaporated in vacuo and the residue was chromatographed on silica gel, eluting with 5:1 (by volume) methylene chloride-/ethyl acetate. The fractions containing the desired esters of N t-butoxycarbonyl-L phenylalanine were combined and evaporated in vacuo to obtain 2.5 g. of a white amorphous foam.

To this foam was added 30 ml. of anhydrous trifluoroacetic acid at 0° C. and the mixture stirred in an ice bath for 30 minutes during which time solution occurred. The trifluoroacetic acid was removed by evaporation in vacuo on a rotary evaporator without external warming of the flask. The residual solid was dissolved in cold methylene chloride and washed with cold 1% (w/w) aqueous sodium bicarbonate solution until neutral to pH test paper. The neutral organic layer was dried ($MgSO_4$) and the solvent was evaporated to obtain 1.6 g. of pale yellow gum. The gum was purified by chromatography on 40 g. of Merck 230–400 mesh silica gel eluting with 35:1 (v/v) ethyl acetate/methanol. Fractions containing the L-phenylalanine ester of the $\alpha$-enantiomer and those containing the L-phenylalanine ester of $\beta$-enantiomer were separated, and evaporated to dryness in vacuo to obtain 636 mg. and 474 mg., respectively.

A stirred solution of 625 mg. of the L-phenylalanine ester of $\beta$-enantiomer in 10 ml. of methanol at room temperature was treated with 10% aqueous sodium hydroxide until cloudy and was then stirred for 30 minutes at room temperature. The methanol was removed by evaporation under reduced pressure and 10 ml. of water was added. The aqueous suspension was extracted with methylene chloride and the combined organic layers were dried over magnesium sulfate. Evaporation of the solvent gave a pale yellow gum which was dissolved in acetone (5 ml.) and treated with an excess of ethereal hydrogen chloride from which the hydrochloride salt of the dextrorotatory $\alpha$-enantiomer crystallized as platelets, 380 mg., M.P. 251°–255° C. $[\alpha]_D^{20} = +32.2°$ (C=1.67 in methanol).

Hydrolysis of the L-phenylalanine ester of the $\beta$-enantiomer (474 mg. obtained above) similarly provided the levorotatory $\beta$-enantiomer of 8-fluoro-5-(p-fluorophenyl)-2-[4-hydroxy-4-(p-fluorophenyl)butyl]-2,3,4,4a,5,9b-hexahydro-1H-pyrido[4,3-]indole hydrochloride, M.P. 252°–255° C., $[\alpha]_D^{20} = -33.0°$ (C=1.67 in methanol).

HPLC analysis showed a $\alpha$-enantiomer and the $\beta$-anantiomer were each of 99% or higher purity.

B. Resolution of $\gamma\delta$-Diastereomer into $\gamma$- and $\delta$-Enantiomers The $\gamma\delta$-diastereomer of trans-8-fluoro-5-(p fluorophenyl)-2-[4-hydroxy-4-(p-fluorophenyl)butyl]-2,3,4,4a,5,9b-hexahydro-1H-[4,3-b]indole was reacted with N-t-butoxycarbonyl-L-phenylalanine, the resulting t-boc-L-phenylalanine ester reacted with trifluoroacetic acid to remove the amino protecting (t boc) group, and the amino acid esters chromatographed to separate the L phenylalanine esters of the $\gamma$-enantiomer and the $\delta$-enantiomer as described in Part A above. The separated $\gamma$- and $\delta$-esters were then hydrolyzed separately and purified to obtain the dextrorotatory $\gamma$-enantiomer and the levororatory $\delta$-enantiomer as the hydrochloride salts by the procedure described in Part A above.

| $\gamma$-enantiomer: | M.P.$_{20}$240–248° C. (dec.) |
|---|---|
| | $[\alpha]_D = +3.1°$ (c = 1.67, methanol) |
| $\delta$-enantiomer: | M.P.$_{20}$240–248° C. (dec.) |
| | $[\alpha]_D = -2.7°$ (c = 1.67, methanol |

HPLC analysis showed that the $\gamma$-enantiomer was about 95% pure and the $\delta$-enantiomer was of 97% purity. The lower purity of these enantiomers is expected in view of the above-mentioned contamination of the $\gamma\delta$-diastereomer with $\alpha\beta$-diastereomer.

EXAMPLE 15

A. D(−)-N-carbamoylphenylalanine

To a suspension of 16.52 g. (0.10 mole) D(+)-phenylalanine in 75 ml. of water was added 12.4 g. (0.10 mole) of sodium carbonate hydrate. To the resulting solution was added, with stirring, 12.17 g. (0.15 mole) of potassium cyanate and the mixture was heated on the steam bath (internal temperature 85°–90° C.) for 1.5 to 2.0 hours. After cooling in an ice bath, the reaction mixture was carefully acidified to pH 1-2 with concentrated hydrochloric acid. The precipitate was collected by filtration, washed with ice water then with ethyl ether to obtain 15 g. of crude product. This was recrystallized by dissolving in 250 ml. of warm methanol, diluting with 400 ml. of water, allowing to cool slowly to room temperature, then refrigerated until precipitation was complete. The product was obtained as white opaque needles in 58% yield after recrystallization, M.P. 203°–204° C. (dec.), $[\alpha]_D^{20}$ (−) 40.7° (methanol).

B. L(+)-N-carbamoylphenylalanine

Employing L(−)-phenylalanine in the above procedure in place of the D(+)-isomer afforded L(+)-N carbamoylphenylalanine in 42% yield after recrystallization, M.P. 205–207° C. (dec.), $[\alpha]_D^{20}$ (+) 39.0° (methanol).

EXAMPLE 16

Resolution of dl-trans-8-fluoro-5-(p-fluorophenyl)-2,3,4,4a,5,9b-hexahydro-1H-pyrido[4,3-b]indole

A. Resolution of Enantiomeric N-carbamoylphenylalanine Salts.

1. To one equivalent of dl-trans 8-fluoro-5-(p-fluorophenyl)-2,3,4,4a,5,9b-hexahydro-1H-pyrido[4,3-b]indole free base dissolved in a minimum amount of ethanol was added one equivalent of L(+) N carbamoylphenylalanine. The mixture was heated on a steam bath while adding additional ethanol until a homogeneous solution was obtained. The solution was allowed to cool to room temperature and the precipitated white needles of the L(+) N carbamoylphenylalanine salt of the (−) enantiomer of the free base were collected by filtration and dried, M.P. 207°–209° C., $[\alpha]_D^{20}$ −5.9° methanol.

2. The mother liquor from above was evaporated to dryness, the residue partitioned between aqueous sodium carbonate and ethyl acetate, the organic layer dried over magnesium sulfate and evaporated in vacuo to afford a residual oil. The oil was dissolved in a small amount of ethanol and treated with one equivalent of D(−)-N-carbamoylphenylalanine. The mixture was warmed on the steam bath while adding more ethanol until solution was complete. The solution was cooled and worked up as above to afford a 92% yield of crude D(−)-N-carbamoylphenylalanine salt of the (+) enantiomer of the free base. This was recrystallized from ethanol (75 ml./g.) in 65% overall yield, M.P. 209°–211° C., $[\alpha]_D^{20}$ = +6.6° (methanol).

B. Isolation of Enanantiomeric Free Base Hydrochloride Salts

1. The enantiomeric N-carbamoylphenylalanine salt obtained in Part A, 1 was partioned between aqueous saturated sodium bicarbonate and ethyl acetate, the organic layer dried over magnesium sulfate and concentrated in vacuo without heating. The residual oil was dissolved in anhydrous ethyl ether (50–100 ml./g.) and dry hydrogen chloride gas is passed over the surface of the solution with swirling to afford a white precipitate. The excess hydrogen chloride and ether are removed by evaporation at reduced pressure and ambient temperature to give (−)-trans-8-fluoro-5-(p-fluorophenyl)-2,3,4,4a,5,9b-hexahydro-1H-pyrido[4,3-b]indole hydrochloride in about 96% yield. This was recrystallized by dissolving in a minimum amount of boiling ethanol, and addition of ethyl ether until the solution becomes turbid. The product was obtained as small white crystals (75% recovery), M.P. 258°–260° C., $[\alpha]_D^{20}$ (−)40.9° (methanol).

2. In the same manner, (+) trans 8-fluoro-5-(p-fluorophenyl)-2,3,4,4a,5,9b-hexahydro-1H-pyrido[4,3-b]indole was obtained from the salt provided above in Part A,2, in 96% crude yield and 75% recovery upon recrystallization, M.P. 260°–262.5° C., $[\alpha]_D^{20}$(+)39.2° (methanol).

EXAMPLE 17

Resolution of dl-4-hydroxy-(p-fluorophenyl)-butyric acid

A. Commercial γ-(p-fluorophenyl)-γ-butyrolactone, 18.0 g. (0.10 mole) was added to a solution of 14.0 g. (0.35 mole) of sodium hydroxide in 100 ml. of water and the mixture heated at reflux for 40 minutes. After cooling to 0° C., 70 ml. of 6N-hydrochloric acid was added at 0°–15° C. for one hour. The white solid which formed was filtered, washed with pentane and air dried to afford racemic-4-hydroxy-4-(p-fluorophenyl)butyric acid, 18.43 g., (93% yield). When heated to temperatures of about 100° C., the hydroxy acid was converted back to the starting lactone.

B. The hydroxy acid obtained above, 18.43 g. (0.093 mole) was dissolved in 200 ml. of ethyl acetate with gentle warming and to the solution was added a solution of 15.04 g. (0.91 mole) of d-ephedrine, $[\alpha]_{578}$=(+)11.4 (acetone), in 80 ml. of ethyl acetate. The mixture was stirred at room temperature over night during which time a crop of crystals formed, was removed by filtration and air dried to obtain 18.3 g., M.P. 97°–99° C. This material was recrystallized by dissolving it in a minimum amount of hot ethyl acetate and allowing to stand at ambient temperature over night. After three such recrystallizations, 8.9 g. of the d-epedrine salt of 1-4-hydroxy-4-(p fluorophenyl)butyric acid, M.P. 105.5°–106.5° C. was obtained.

This product was taken up in a mixture of ice cold 5% hydrochloric acid (300 ml.) and ethyl acetate (150 ml.), the aqueous phase extracted five times with 100 ml. portions of cold ethyl acetate, the combined organic extracts washed with saturated brine and dried ($MgSO_4$). The solvent was evaporated in vacuo to a small volume to obtain 3.8 g. of the l-enantiomer as crystals, M.P. 98°–104° C., $[\alpha]_{578}$=(−)32.6°. Upon recrystallization from methylene chloride, the optical rotation was $[\alpha]_{578}$=(−)33.4° C. An additional 0.4 g. of product was obtained from the combined filtrates from the three crystallizations above.

C. The first filtrate from Part B above was evaporated to dryness in vacuo to obtain 15.5 g. of residue which was taken up in a mixture of cold 5% hydrochloric acid and ethyl acetate and the aqueous phase extracted with fresh ethyl acetate. The combined organic layers were dried ($MgSO_4$) and solvent evaporated to obtain 8.19 g. (0.040 mole) of hydroxy acid. This was taken up in fresh ethyl acetate (100 ml) and a solution of 6.60 g. (0.040 ml.) of l-ephedrine in 50 ml. of ethyl acetate was added. The mixture was stirred over night at room temperature and the precipitated salt recovered by filtration and air dried, 12.2 g., M.P. 101°–104° C. The salt was recrystallized four times from ethyl acetate to obtain 8.2 g. of the l-ephedrine salt of d-4-hydroxy-4-(p-fluorophenyl))butyric acid, M.P. 105.5°–107° C. This salt was decomposed by treatment with ice cold 5% hydrochloric acid and ethyl acetate as described in Part B above, to provide 4.0 g. of the d-hydroxy acid, M.P. 98°–104° C., $[\alpha]_{578}=(+)33.1°$.

EXAMPLE 18 d(+)-and l(−)-γ(p-Fluorophenyl)-γ-butyrolactone

A. l(−)-4-hydroxy-4-(p-fluorophenyl) butyric acid provided in Part B of Example 17, (250 mg., 1.26 mmole) was dissolved in 15 ml. of ethyl acetate and several crystals of p-toluenesulfonic acid was added. The mixture was heated at reflux for 25 minutes, cooled to room temperature, washed with saturated brine and dried (MgSO$_4$). The solvent was evaporated to yield 216 mg. (91%) of the l-lactone as a white solid, M.P. 52°–54° C., $[\alpha]_{578}=(-)4.0°$.

B. d(+)-4-hydroxy-4-(p-fluorophenyl) butyric acid when treated in the same manner afforded the d-lactone, $[\alpha]_{578}=(+)4.3°$.

EXAMPLE 19

5-(p-Fluorophenyl)-2-hydroxytetrahydrofuran

A. To a solution of 594 mg. (3.0 mmole) of d(+)-4-hydroxy-4-(p-fluorophenyl) butyric acid, $[\alpha]_{578}=33.1°$ (acetone). in 25 ml. of ethyl acetate was added 10 mg. of p-toluenesulfonic acid hydrate and the mixture heated at reflux for 30 minutes. The solvent was evaporated in vacuo, chasing the last traces of solvent with 20 ml. of toluene. The residual lactone was taken up in 30 ml. of fresh toluene and cooled under a nitrogen atmosphere to −74° C. by means of a dry ice/acetone bath. To this was added, dropwise over a 30 minute period, 4.2 ml. (3.3 mmole) of 0.804 M diisobutylaluminum hydride (Dibal) in hexane while maintaining the mixture below −72° C. The reaction mixture was stirred for an additional 30 minutes at −72° to −74° C., quenched with methanol and warmed to 0° C. The solvent was evaporated in vacuo, residue triturated four times with boiling methanol and the methanol filtered. The combined methanol extracts were evaporated to a viscous pale yellow oil which was one spot by TLC. It was used as an intermediate without further purification.

B. Levorotatory 4-hydroxy-4-(p-fluorophenyl) butyric acid obtained above in Example 17 and the commercially available racemic compound were covered, respectively, to the corresponding enantiomeric and racemic title compounds by the procedure of Part A.

EXAMPLE 20

Starting with the appropriate d-, l-, or dl-4-hydroxyarylbutyric acid or 5-hydroxy-5-arylvaleric acid, or the corresponding lactone, in the procedure of Example 19, Part A, provides the following compounds in like manner.

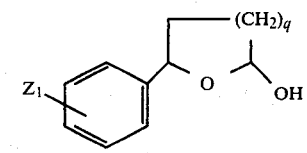

| When q is 1: Z$_1$ | When q is 2: Z$_1$ |
|---|---|
| H | H |
| o-F | p-F |
| m-F | o-F |
| p-OCH$_3$ | p-OCH$_3$ |
| m-OCH$_3$ | m-OCH$_3$ |

The requisite 6-aryl-6-hydroxyvaleric acid lactones are prepared by the method of Colonge, et. al., *Bull. Soc. Chim. France.*, 2005–2011 (1966); *Chem. Abstr.*, 65, 18547d (1966).

EXAMPLE 21

Chiral synthesis of enantiomers of 8-fluoro-5-(p-fluorophenyl)-2-[4-hydroxy-4-(p-fluorophenyl)butyl]-2,3,4,4a,5,9b-hexahydro-1H-pyrido[4,3-b]indole α-Enantiomer 5-(p-fluorophenyl)-2-hydroxytetrahydrofuran obtained from d(+)-4-hydroxy-4-(p-fluorophenyl) butyric acid in Example 19, Part A, 230 mg., was dissolved in 30 ml. of methanol. Dextrorototary 8-fluoro-5-(p-fluorophenyl)-2,3,4,4a,5,9b-hexahydro-1H-pyrido[4,3-b]indole free base, 404 mg. (1.25 mmole) was added, the mixture stirred for 15 minutes, 150 mg. of 10% palladium-on-carbon catalyst was added and the stirred mixture hydrogenated at atmospheric pressure. When hydrogen uptake ceased, the catalyst was removed by filtration and the solvent evaporated in vacuo. The residue was partitioned between ethyl acetate and 10% aqueous sodium hydroxide. The aqueous layer was extracted again with ethyl acetate, the combined extracts dried (MgSO$_4$) and evaporated to dryness in vacuo. The residue was chromatographed on 20 g. of silica gel and eluted with ethyl acetate. The fractions containing the desired product was combined, evaporated to dryness, taken up in ethyl ether and converted to hydrochloride salt by addition of ethereal hydrogen chloride. Yield, 144 mg., M.P. 248°–252° C., $[\alpha]_D^{22}=(+)30.1°$ (methanol). 97.5% pure by high pressure liquid chromatography analysis.

β-Enantiomer

To a solution of 53 mg. (0.95 mmole) of potassium hydroxide in 50 ml. of methanol under a nitrogen atmosphere was added 613 ml. (1.90 mmole) oflevorotatory 8-fluoro-5-(p-fluorophenyl)-2,3,4,4a,5,9b-hexahydro-1H-pyrido[4,3-b]indole hydrochloride, $[\alpha]_D=(-)40.9$ (methanol) and the mixture stirred until solution was complete. To the solution was added 346 mg. (1.90 mmole) of levorotatory 5-(p-fluorophenyl)2-hydroxytetrahydrofuran (from Example 19, Part B), dissolved in a small volume of methanol and the resulting solution stirred for 15 minutes at room temperature. The solution was cooled to 5° C. and 120 mg. (1.90 mmole) of sodium cyanoborohydride in a small amount of methanol was added over 20 minutes. The reaction mixture was stirred at room temperature for 45 minutes, then 250 mg. of potassium hydroxide was added and stirred until dissolved. The solvent was evaporated in vacuo and the residue partitioned between ethyl acetate and water. After reextraction of the aqueous phase, the combined organic extracts were dried (MgSO$_4$) and evaporated in vacuo to provide 1.014 g. of oil. This was chromatographed on 30 g. of silica gel as described above to obtain 653 mg. of the desired product as an oil. The oil was converted to the hydrochloride salt, as above, 400 mg., M.P. 252°–257° C. (dec.), $[\alpha]_D^{23}=(-)33.7°$ (methanol) which was found to be 99% pure β-enantiomer by HPLC. Reworking the mother liquors afforded 80 mg. of a second crop, M.P. 254°–258° C. (dec.). Total yield 56%.

γ-Enantiomer

In 23 ml. of methanol were dissolved 2.07 mg. (6.4 mmole) of d(+)-8-fluoro-5-(p-fluorophenyl)-2,3,4,4a,5,9b-hexahydro-1H-pyrido [4,3-b]indole hydrochloride, $[\alpha]_D^{20}(+)39°$, and 1.3 g. (7.1 mmole) of levorotatory 5-(p-fluorophenyl)-2-hydroxytetrahydrofuran and the solution stirred under a nitrogen atmosphere at room temperature for 15 minutes. Five percent palladium-on-carbon catalyst, 300 mg., was added and the mixture hydrogenated at atmospheric pressure for 3 hours. The reaction mixture was worked up as described above for the α-enantiomer to obtain 2.4 g. of crude product as a yellow foam. The foam was dissolved in 40 ml. of acetone and this was added to 20 ml. of ethyl ether saturated with hydrogen chloride. The mixture was filtered after standing at room temperature for two hours to obtain 980 mg. of hydrochloride salt. The filtrate was evaporated to provide 1.7 g. of foam. These were chromatographed separately on silica gel and the product fractions treated again with hydrogen chloride to obtain, respectively, 140 mg., $[\alpha]_D=(+)1.4°$ (methanol) and 800 mg., $[\alpha]_D=(+)1.7°$ (methanol). Both crops had a melting point of 254°–256° C. Each were found to be 98% pure γ-enantiomer by HPLC.

δ-Enantiomer

1(−)-8-Fluoro-5-(p-fluorophenyl)2,3,4,4a,5,9b-hexahydro-1H-pyrido[4,3-b]indole hydrochloride, $[\alpha]_D=(-)40.9°$, (968 mg., 3.0 mmole) and an equimolar amount of dextrorotatory 5-(p fluorophenyl) 2-hydroxytetrahydrofuran obtained by the procedures of Example 16, Part B-1 and Example 19, Part B, were reacted by the procedure described above for the α-enantiomer to provide 1300 mg. of crude δ-enantiomer as a pale yellow gum. The gum was converted to hydrochloride salt, 835 mg., (57%), M.P. 240°–250° C. This was chromatographed on 30 g. of silica gel and the eluted product fraction evaporated and again treated with ethereal hydrogen chloride to provide 610 mg., M.P. 257°–260° C., $[\alpha]_D=(-)2.7°$ (methanol) which assayed 98% pure by HPLC.

EXAMPLE 22

Employing the procedure of Example 16, the following dl-trans-5-aryl-2,3,4,4a,5,9b-hexahydro-1H pyrido[4,3-b]indoles were each resolved into dextrorotatory and levorotatory enantiomers and isolated as the hydrochloride salt.

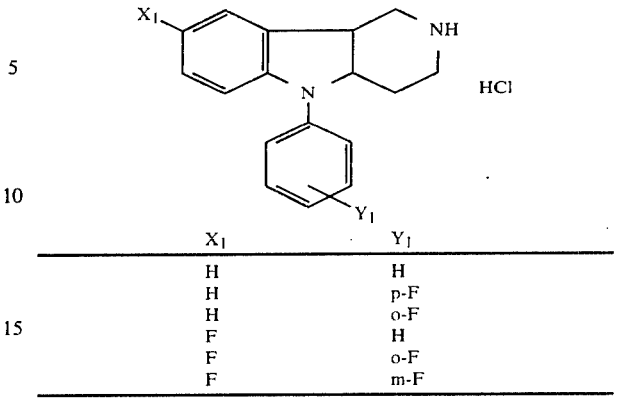

| X$_1$ | Y$_1$ |
|---|---|
| H | H |
| H | p-F |
| H | o-F |
| F | H |
| F | o-F |
| F | m-F |

EXAMPLE 23

Starting with the racemic or enantiomeric 5-aryl-2,3,4,4a,5,9b-hexahydro-1H-pyrido[4,3-b]indole hydrochlorides provided above and the d-, l- or dl- isomer of a 5-aryl-2-hydroxytetrahydrofuran or 6-aryl-2-hydroxytetrahydropyran, each of the enantiomers and diastereomers of the following formula are prepared by the procedure of Example 21.

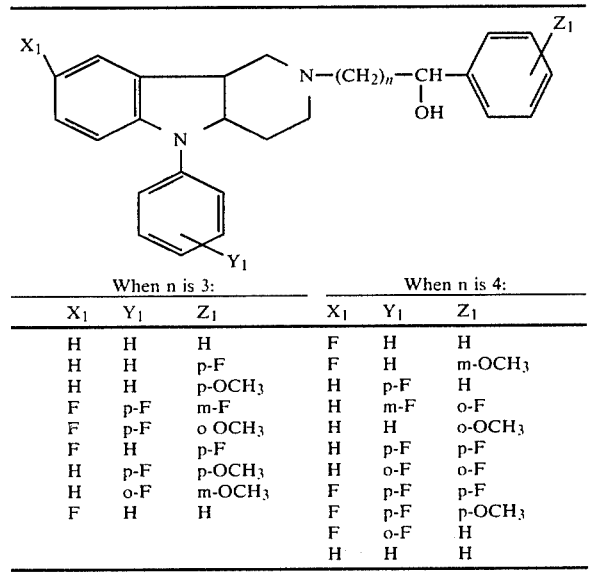

| When n is 3: | | | When n is 4: | | |
|---|---|---|---|---|---|
| X$_1$ | Y$_1$ | Z$_1$ | X$_1$ | Y$_1$ | Z$_1$ |
| H | H | H | F | H | H |
| H | H | p-F | F | H | m-OCH$_3$ |
| H | H | p-OCH$_3$ | H | p-F | H |
| F | p-F | m-F | H | m-F | o-F |
| F | p-F | o OCH$_3$ | H | H | o-OCH$_3$ |
| F | H | p-F | H | p-F | p-F |
| H | p-F | p-OCH$_3$ | H | o-F | o-F |
| H | o-F | m-OCH$_3$ | F | p-F | p-F |
| F | H | H | F | p-F | p-OCH$_3$ |
| | | | F | o-F | H |
| | | | H | H | H |

When catalytic amounts of platinum, rhodium, ruthenium or Raney nickel catalyst are employed in place of palladium catalyst, and the reductive alkylation described in Example 21 for the α-enantiomer is carried out at temperatures of from −10° C. to 50° C. and at pressures of from atmospheric pressure up to 10 atmospheres employing the above-mentioned lactols and 5-aryl-2,3,4,4a,5,9b-hexahydro-1H-pyrido[4,3-b]indoles, the above compounds are obtained in a like manner.

When the reductive alkylation employing the above reactants are repeated, but employing sodium cyanolborohydride as the reducing agent as described in Example 21 for the β-enantiomer and reaction temperatures of from −10° C. to 50° C., the above products are similarly obtained.

EXAMPLE 24

When each of the compounds provided in Examples 21 and 23 are oxidized by the procedure of Example 10, the product obtained is of the following structure.

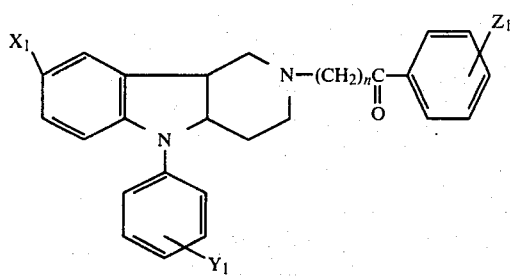

When the starting alcohols of formula (I,M=CHOH) have been derived from a dextrorotatory or levorotatory 5-aryl-2,3,4,4a,5,9b-hexahydro-1H-pyrido[4,3-b]indole, the above products are obtained with retention of configuration in the pyrido[4,3b]indole moiety as evidenced by the optical rotation of the products. Starting alcohols of formula (l,m=CHOH), wherein, for example, the pyrido[4,3-b]indole moiety is dextrorotatory and the 2-substituent is either d-, l or dl, afford the same product.

EXAMPLE 25

A. dl-trans-8-Fluoro-5-(p-fluorophenyl) 2-[4-hydroxy-4-(p-fluorophenyl(butyl]-2,3,4,4a,5,9b-hexahydro-1H-pyrido [4,3-b]indole acetate Five grams of di-trans-8-fluoro-5-(p-fluorophenyl)-2-[4-hydroxy-4-(p-fluorophenyl)butyl]-2,3,4,4a,5,9b-hexahydro-1H-pyrido [4,3-b]indole hydrochloride in 75 ml. of water is treated with 3 ml. of water containing 1.0 g. of sodium hydroxide, and the liberated free base extracted into 150 ml. of diethyl ether. The ether layer is separated, dried over magnesium sulfate and treated with 1 ml. of glacial acetic acid. The organic solvent and excess acetic acid are removed under reduced pressure and the residue triturated with hexane and filtered.

B. Enantiomeric trans 8-Fluoro-5-(p fluorophenyl) 2-[4-hydroxy-4-(p-fluorophenyl)butyl]-2,3,4,4a,5,9b-hexahydro-1H pyrido 84,3-b]indole citrate The hydrochloride salt of the γ-enantiomer of the title compound provided in Example 21 was converted to free base by the above procedure. The ether was evaporated and the free base taken up in ethanol. To the ethanol solution was added an equimolar amount of anhydrous citric acid dissolved in ethanol and the resulting mixture stirred for 15 minutes. The solvent was removed in vacuo to provide the citrate salt.

In a similar manner pharmaceutically acceptable acid addition salts are obtained by employing hydrobromic, sulfuric, phosphoric, maleic fumaric, succinic, lactic, tartaric, gluconic, saccharic or p-toluenesulfonic acid and one of the compounds of formula (I) by the above procedures.

EXAMPLE 26

Antagonism of Amphetamine Stereotypy in Rats Test Procedures and Results

The effects of the compounds of the present invention on prominent amphetamine-induced symptoms were studied in rats by a rating scale modeled after the one reported by Quinton and Halliwell, and Weissman. Groups of five rats were placed in a covered plastic cage measuring approximately 26 cm.×42 cm.×16 cm. After a brief period of acclimation in the cage, the rats in each group were treated subcutaneously (s.c.) with the test compound. They were then treated 1, 5 and 24 hrs. later with d-amphetamine sulfate, 5 mg./kg. intraperitoneally (i.p.). One hour after amphetamine was given each rat was observed for the characteristic amphetamine behavior of moving around the cage. On the basis of dose-response data after amphetamine it was possible to determine the effective dose of the compound necessary to antagonize or block the characteristic amphetamine behavior of cage movement for fifty percent of the rats tested ($ED_{50}$). The time of rating chosen coincides with the peak action of amphetamine which is 60–80 min. after treatment with this agent.

Employing the above-described procedure, the following 4a,9b-trans compounds were tested for their ability to block the behavior effects of amphetamine, the results being reported as the $ED_{50}$ in mg./kg. at the indicated times:

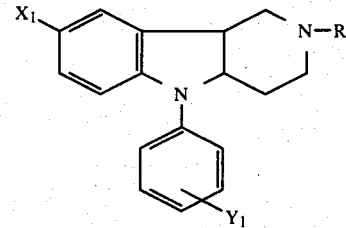

A. The following results were obtained on the mixture of diastereomers for those compounds wherein R contains a secondary alcohol group and on the single diastereomer of the other 4a, 9b-trans hexahydropyrido-indoles.

| $X_1$ | $Y_1$ | R | $ED_{50}$ (mg./kg.) | | |
|---|---|---|---|---|---|
| | | | 1 Hr. | 5 Hr. | 24 Hrs. |
| H | H | $C_6H_5CH-(CH_2)_3-$<br>\|<br>CH | 0.032–0.1 | 0.032–0.1 | 0.1–0.32 |
| H[a] | H | p-$FC_6H_4CH-(CH_2)_3-$<br>\|<br>CH | 0.1–0.32 | 0.1–0.32 | 0.1–0.32 |
| H | H | p-$CH_3OC_6H_4CH-(CH_2)_3-$<br>\|<br>CH | 0.1–0.32 | 0.1–0.32 | ~1.0 |
| H | H | p-$FC_6H_4C-(CH_2)_3-$<br>\|\|<br>O | ~0.32 | 0.1–0.32 | ~0.32 |

-continued

| $X_1$ | $Y_1$ | R | ED$_{50}$ (mg./kg.) | | |
|---|---|---|---|---|---|
| | | | 1 Hr. | 5 Hr. | 24 Hrs. |
| F | p-fluoro | C$_6$H$_5$CH—(CH$_2$)$_3$—<br>\|<br>OH | 0.1–0.32 | 0.1–0.32 | <0.32 |
| F | o-fluoro | p-FC$_6$H$_4$CH—(CH$_2$)$_3$—<br>\|<br>OH | <0.32 | <0.32 | <0.32 |
| F | p-fluoro | p-FC$_6$H$_4$CH—(CH$_2$)$_3$—<br>\|<br>OH | 0.032–0.1 | 0.032–0.1 | 0.032–0.1 |
| F | p-fluoro | p-CH$_3$OC$_6$H$_4$CH—(CH$_2$)$_2$—<br>\|<br>CH | 0.1–0.32 | <0.1 | <0.32 |
| F | p-fluoro | p-FC$_6$H$_4$C—(CH$_2$)$_3$—<br>\|\|<br>O | <1.0 | <1.0 | <1.0 |
| H[b] | H | H | 3.2–32 | >3.2 | >32 |
| H[b] | H | C$_2$H$_5$ | ~1.0 | >3.2 | NT[c] |
| H[b] | H | C$_6$H$_5$CH$_2$— | ~10 | 3.2–32 | >3.2 |
| H[b] | H | C$_6$H$_5$(CH$_2$)$_3$— | 3.2–10 | 3.2–10 | >10 |
| Navane[d], | po | | 0.32–1.0 | >10 | >32 |

Footnotes
[a] The corresponding 4a,9b-cis analog was found to have an ED$_{50}$ ~56 mg./kg. at 1 hr.
[b] U.S. Pat. No. 3,991,199.
[c] Not tested.
[d] cis-9-[3-(4-Methyl-1-piperazinyl)propylidene]-2-(dimethylsulfonamido)thioxanthene U.S. Pat. No. 3,310,553.

B. The results of tests in which compounds of the invention reported in Part A, above are compared with the corresponding δ-substituted-5-aryl-1,2,3,4-tetrahydropyrido[4,3-b]indoles of U.S. Pat. No. 4,001,263 are summarized below. For each pair the results obtained on the prior art compound (a) are given first and the results for the compound of the invention (b) are given second. Where indicated the test compound was also administered orally (p.o.) and tests were carried out for 48 hours.

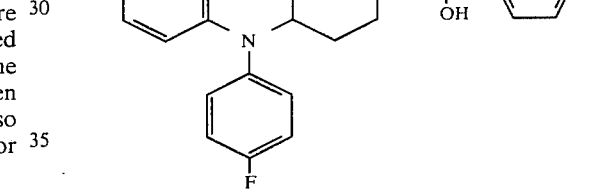

| $X_1$ | $Y_1$ | R | | ED$_{50}$ (mg.kg.) | | | | Rte. of Admin. |
|---|---|---|---|---|---|---|---|---|
| | | | | 1 Hr. | 5 Hrs. | 24 Hrs. | 48 Hrs. | |
| H | H | C$_6$H$_5$CH—(CH$_2$)$_3$—<br>\|<br>OH | (a) | 3.2–10 | 3.2–10 | >10 | — | i.p. |
| | | | (b) | 0.032–0.1 | 0.032–0.1 | 0.1–0.32 | — | i.p. |
| F | p-F | p-FC$_6$H$_4$CH—(CH$_2$)$_3$—<br>\|<br>OH | (a) | 0.1–0.32 | 0.1–3.2 | 1.0–3.2 | 3.2–1.0 | i.p. |
| | | | (b) | 0.032–0.1 | 0.032–0.1 | 0.032–0.1 | 0.1–0.32 | i.p. |
| | | | (a) | 1–3.2 | 0.32–1.0 | 1.0–3.2 | — | p.o. |
| | | | (b) | 0.32–1.0 | 0.1–0.32 | 0.1–0.32 | — | p.o. |
| F | p-F | p-FC$_6$H$_4$C(CH$_2$)$_3$—<br>\|\|<br>O | (a) | 3.2–10 | >10 | — | — | i.p. |
| | | | (b) | <1.0 | <1.0 | <1.0 | — | i.p. |
| F | o-F | p-FC$_6$H$_4$CH—(CH$_2$)$_3$—<br>\|<br>OH | (a) | 0.32–1 | 1–3.2 | >10 | — | i.p. |
| | | | (b) | 0.1–0.32 | ca. 0.1 | ca. 0.1 | — | i.p. |
| | | | (b) | <1 | <1 | <1 | — | p.o. |

C. Test results expressed as micrograms/kilograms, obtained on the diastereomers αβ and γδ separated in Example 13 and each of the enantiomers α, β, γ and δ resolved by the procedure of Example 14 are shown below. In each case the compounds are of the formula

| Compound | $[\alpha]_D$ | ED$_{50}$(micrograms/kilograms) | | |
|---|---|---|---|---|
| | | 1 Hr. | 5 Hrs. | 24 Hrs. |
| αβγδ<br>(mixture of diastereomers) | — | 32–100 | 32–100 | 32–100 |
| αβ | — | — | 32–100 | 32–100 |
| α | +32.2° | 120 | 32–100 | 32–100 |
| β | −33.0 | >1000 | >1000 | >1000 |
| γδ | — | — | 32–100 | 32–100 |
| γ | +3.1 | 180 | 32–100 | 32–100 |
| δ | −2.7 | >1000 | 560 | 320–1000 |

D. ED$_{50}$ values (mg./kg.) obtained with purified α, β, γ and δ enantiomers of the formula shown in Part C, above, but obtained by synthesis as described in Example 21 are summarized below. The tests were carried out for 72 hours.

| Enantiomers of Formula Shown in Part C | $[\alpha]_D$ | ED$_{50}$ (mg./kg.) | | | | |
|---|---|---|---|---|---|---|
| | | 1 Hr. | 5 Hrs. | 24 Hrs. | 48 Hrs. | 72 Hrs. |
| α | +30.1° | 0.023 | 0.014 | 0.033 | ca. 1 | >10 |
| β | −33.7° | >10 | 5.7 | >10 | >10 | >10 |
| γ | +1.7° | 0.178 | 0.045 | 0.018 | ca. 1 | >1 |
| δ | −2.7° | >10 | 5.7 | >10 | >10 | >10 |

EXAMPLE 27

Inhibitors of $^3$H-Spiroperidol Binding to Dopamine Receptors

Test Procedures and Results

The relative affinity of drugs for dopamine binding sites have been shown to correlate with their relative pharmacological potencies in affecting behavior presumably mediated by dopamine receptors, see e.g., Burt et. al., *Molecular Pharmacol.*, 12, 800–812 (1976) and references cited therein. A superior binding assay for neuroleptic receptors has been developed by Leyson et. al, *Biochem Pharmacol*, 27, 307–316 (1978) using $^3$H-spiroperidol (spiperone) as the labeled ligand. The procedure used was a follows:

Rats (Sprague-Dawley CD males, 250–300 g., Charles River Laboratories, Wilmington, MA) were decapitated, and brains were immediately dissected on an ice-cold glass plate to remove corpus striatum (~100 mg./brain). Tissue was homogenized in 40 volumes (1 g.+40 ml.) of ice-cold 50 mM. Tris (tris [hydroxymethyl]aminomethane; (THAM) ·HCl buffer pH 7.7. The homogenate was centrifuged twice at 50,000 g. (20,000 rpm) for 10 minutes with rehomogenization of the intermediate pellet in fresh THAM buffer (same volume). The final pellet was gently resuspended in 90 volumes of cold, freshly prepared (<1 week old) 50 mM Tris buffer pH 7.6 containing 120 mM NaCl (7.014 g./l.), 5 Mm KCl (0.3728 g./l.), 2 mM CaCl$_2$ (0.222 g./l.), 1 mM MgCl$_2$ (0.204 g./l/), 0.1% ascorbic acid (1 mg./ml.) and 10 μM pargyline (100 μl. stock/100 ml. buffer; stock=15 mg./10 ml. DDW). Ascorbic acid and pargyline were added fresh daily. The tissue suspension was placed in a 37° C. water bath for 5 minutes to insure inactivation of tissue monoamine oxidase and then kept on ice until used. The incubation mixture consisted of 0.02 ml. inhibitor solution, 1.0 ml. tissue homogenate and 0.10 ml. label ($^3$H-spiroperidol, New England Nuclear 23.6 Ci/mmole), prepared so as to obtain 0.5 nM in the final incubation medium (usually diluted 2.5 μl. stock→17 ml. DDW**). Tubes were incubated in sequence for 10 minutes at 37° C. in groups of three, after which 0.9 ml. of each incubation tube was filtered through Whatman GF/B filters using a high vaccum pump. Each filter was placed in a scintillation vial, 10 ml. of liquid scintillation fluor was added and each vial was vigorously vortexed for about five seconds. Samples were allowed to stand over night, until filters were translucent, vortexed again and then counted 1.0 minute for radioactivity. Binding was calculated as fentamoles (10$^{15}$ moles) of $^3$H-spiroperidol bound per mg. protein. Controls (vehicle or 1 butaclamol, 10$^{-7}$ M; 4.4 mg. dissolved in 200 μl. glacial acetic acid, then diluted to 2.0 ml. with DDW for 10$^{-4}$ M stock solution, kept refrigerated), blank (d-butaclamol, 10$^{-7}$ M; 4.4 mg./2 ml. for 10$^{-4}$ M stock solution, same protocol as 1-butaclamol), and inhibitor solutions were run in triplicate. The concentration reducing binding by 50% (IC$_{50}$) was estimated on semi-log paper. Insoluble drugs were dissolved in 50% ethanol (1% ethanol incubation).

**DDW=Double Distilled Water.

The results obtained with the various forms of trans 8-fluoro-5-(p-fluorophenyl)-2-[4-hydroxy-4(p-fluorophenyl)butyl]-2,3,4,4,a,5,9b-hexahydro-1H-pyrido[4,3-]indole hydrochloride are summarized in the table below.

| Compound | Inhibition of $^3$H-Spiroperidol Binding, mM IC$_{50}$ |
|---|---|
| Mixed αβ and γδ diastereomers of Example 3 | 21 |
| αβ-diastereomer of Example 13 | 23 |
| Dextrorotatory α-enantiomer of Example 14 | 22 |
| Levorotatory β-enantiomer of Example 14 | 1800 |
| γδ-diasteriomer of Example 13 | 23 |
| Dextrorotatory γ-enantiomer of Example 14 | 25 |
| Levorotatory δ-enantiomers of Example 14 | 350 |

EXAMPLE 28

Tablets

A tablet base is prepared by blending the following ingredients in the proportion by weight indicated:
Sucrose, U.S.P: 80.3
Tapioca starch: 13.2
Magnesium stearate: 6.5

Into this tablet base there is blended a sufficient amount of the γ-enantiomer of trans-8-fluoro-5-(p fluorophenyl)-2-[4-(p-fluorophenyl(-4-hydroxybutyl]-2,3,4,4a,5,9b-hexahydro-1H pyrido[4,3-b]indole hydrochlorine to provide tablets containing 1.0, 2.5. 5.0 and 10 mg. of active ingredient per tablet. The compositions are each compressed into tablets, each weighing 360 mg., by convenient means.

EXAMPLE 29

Capsules

A blend is prepared containing the following ingredients:
Calcium carbonate, U.S.P.: 17.6
Dicalcium phosphate: 18.8
Magnesium trisilicate, U.S.P.: 5.2
Lactose, U.S.P.: 5.2
Potato starch: 5.2
Magnesium stearate: 0.8

To this blend is added a second portion of magnesium stearate (0.35 g.) and sufficient trans-5-phenyl-2-(4-hydroxy-4-phenylbutyl)-2,3,4,4a,5,9b-hexahydro-1H-pyrido[4,3-b]indole hydrochloride to provide capsules containing 1.0, 2.5, 5.0 and 10 mg. of active ingredient per capsule. The compositions are filled into conventional hard gelatin capsules in the amount of 350 mg. per capsule.

EXAMPLE 30

Suspension

A suspension of dl-trans 8-fluoro-5-(p-fluorophenyl)-2-[4-hydroxy-4-(methoxy phenyl butyl]-2,3,4,4a,5,9b- hexahydro-1H-pyrido[4,3-b]indole acetate is prepared with the following composition:

| | | |
|---|---|---|
| Effective ingredient | g. | 25.00 |
| 70% aqueous sorbitol | g. | 741.29 |
| Glycerine, U.S.P. | g. | 185.35 |
| Gum acacia (10% solution) | ml. | 100.0 |
| Polyvinylpyrrolidone | g. | 0.50 |

Distilled water, sufficient to make 1 liter. To this suspension, various sweeteners and flavorants are added to improve the palatabitliy of the suspension. The suspension contains approximately 25 mg. of effective agent per milliliter.

EXAMPLE 31

Sesame oil is sterilized by heating to 120° C. for 2 hours. To this oil, a sufficient quantity of pulverized dextrorotatory α-enantiomer of trans-8-fluoro-5-(p-fluorophenyl) 2-[4-(p fluorophenyl)-4-hydroxybutyl]-2,3,4,4a,5,9b-hexahydro-1H-pyrido[4,3-b]indole hydrochloride to make 0.025% suspension by weight. The solid is thoroughly dispersed in the oil by use of a colloid mill. It is then filtered through a 100–250 mesh screen and poured into sterile vials and sealed.

PREPARATION A

2-Benzyl-5-phenyl-1,2,3,4-tetrahydro-γ-carboline

Crude N,N-diphenylhydrazine, 100 g. was made alkaline with aqueous potassium hydroxide and the mixture extracted with ethyl acetate. The organic layer was distilled to afford 39.7 g. (0.216 mole) of N,N-diphenylhydrazine, free base, B.P. 130°–135° C. at 1.1 mm. Hg. This was dissolved in 500 ml. of absolute ethanol and 40.8 g. (0.216 mole) of N-benzyl-4-piperidone in 500 ml. of absolute ethanol was added. The resulting mixture was heated to 65° C. and dry hydrogen chloride gas was added to acidify the mixture which was then heated at reflux for five hours. After standing overnight at room temperature the solvent was evaporated and the residue made alkaline with sodium hydroxide solution, extracted with chloroform, the extracts dried (MgSO$_4$) and evaporated to dryness. The residue was dissolved in ethyl ether, filtered and the filtrate acidified with an ethereal solution of hydrogen chloride to precipitate the crude hydrochloride salt. The salt was converted to the free base by partitioning between aqueous sodium hydroxide and ethyl acetate. The organic layers were dried, concentrated to a small volume and chromatographed on 300 g. of silica gel eluting with 5:1 hexane/ethyl acetate (by volume) to afford 12.0 g. (33%) of the desired product, M.P. 150°–155° C.

PREPARATION B

8-Fluoro-5-(p-fluuorophenyl)-1,2,3,4-tetrahydro-γ-carboline

I. 8-fluoro-2-carbethoxy-1,2,3,4-tetrahydro-γ-carboline

A mixture of 15.9 g. (0.093 mole) of N-carbethoxy-4-piperidone and 15.1 g. (0.093 mole) of p-fluorophenylhydrazine hydrochloride in 150 ml. of ethanol is heated to reflux for 2 hrs. The reddish reaction mixture is cooled and filtered, and the collected solids washed with a small amount of cold 95% ethanol, 21.3 g. (88% yield), m.p. 169°–170° C. The analytical sample is recrystallized from ethanol-water, m.p. 169°–170° C.

Anal. Calc'd for $C_{14}H_{15}O_2N_2F$: C, 64.1; H, 5.8; N, 10.7. Found: C, 63.8; H, 5.8; N, 10.6.

II. 8-fluoro-5-(p-fluorophenyl)-2-carbethoxy-1,2,3,4-tetrahydro-γ-carboline

To 30 ml. of N-methyl-2-pyrrolidone is added 3.45 g. (0.013 mole) of 8-fluoro-2-carbethoxy-1,2,3,4-tetrahydro-γ-carboline, 7.8 g. (0.045 mole) of p-fluorobromobenzene, 4.14 g. (0.014 mole) of cuprous bromide and 1.5 g. (0.014 mole) of sodium carbonate, and the resulting mixture heated in an oil bath at 200° C. for 6 hrs. The mixture is allowed to cool to room temperature overnight, and is then decanted into 300 ml. of water containing 60 ml. of ethylene diamine. Benzene (200 ml.) is added and the two-phase system is filtered through a super-cel pad. The filtrate is subsequently extracted several times with a total of 700 ml. of benzene. The extracts are combined, washed successively with water and a saturated brine solution and dried over anhydrous sodium sulfate. Removal of the solvent provides the crude product as a dark, residual oil.

The crude product in benzene is chromatographed on a silica gel column using 10% ethyl acetate-benzene as the eluate. Fractions 1 through 16, comprised of 10–25 ml. each, and containing p-fluorobromobenzene, are collected and discarded. Fractions 16 to 38 are combined and concentrated in vacuo to an oil which solidifies on standing at 5° C. overnight. The product, 3.5 g. (76% yield), is triturated with pentane and filtered. The analytical sample is recrystallized from pentane, m.p. 118°–120° C.

Anal. Calc'd for $C_{20}H_{18}O_2N_2F_2$: C, 67.4; H, 5.1; N, 7.9. Found: C, 67.4; H, 5.2; N, 7.8.

III. 8-fluoro-5-(p-fluorophenyl)-1,2,3,4-tetrahydro-γ-carboline

A suspension of 3.56 g. (0.01 mole) of 8-fluoro-5-(p-fluorophenyl)-2-carbethoxy-1,2,3,4-tetrahydro-γ-carboline and 8.2 g. (0.146 mole) of potassium hydroxide in 53 ml. of ethanol containing 5 ml. of water is heated to reflux overnight. An additional 3.0 g. of potassium hydroxide is added and the heating continued for 23 hrs. The brownish solution is cooled, concentrated in vacuo to dryness and partitioned between water and diethyl ether. The aqueous layer is further extracted with ether, and the ether layers combined, washed with a saturated brine solution and dried over magnesium sulfate. Removal of the solvent provides the desired product as an orange solid, 2.6 g. m.p. 125°–127° C. The analytical sample is recrystallized from pentane, m.p. 127°–128° C.

Anal. Calc'd for $C_{17}H_{14}N_2F_2$: C, 71.8; H, 5.0; N, 9.9. Found: C, 71.6; H, 5.1; N, 10.2.

The hydrochloride salt is prepared by bubbling hydrogen chloride into a solution of the free base in diethyl ether, m.p. 270°–272° C.

PREPARATION C

2-Benzyl-8-fluoro-5-(p-fluorophenyl)-1,2,3,4-tetrahydro-γ-carboline

To a stirred solution of 1.4 g. (4.9 mmoles) of 8-fluoro-5-(p-fluorophenyl)-1,2,3,4-tetrahydro-γ-carboline and 1.02 g. (7.4 mmoles) of potassium carbonate in 10 ml. of dimethylformamide, heated to 60° C. is added dropwise 1.01 g. (5.9 mmoles) of benzyl bromide in 10 ml. of the same solvent. After heating for one hour, the reaction mixture is decanted into 200 ml. of an aqueous 2% potassium carbonate solution, and the resulting solution subsequently extracted (3×200 ml.) with benzene. The combined extracts are washed successively with water and a saturated brine solution, and dried over magnesium sulfate. The solvent is removed in vacuo and the residual oil which crystallizes on standing is triturated with hexane and filtered.

PREPARATION D

8-Fluoro-5-(p-fluorophenyl)-2-[4-(p-fluorophenyl)-4-hydroxybutyl]-1,2,3,4-tetrahydro-γ-carboline hydrochloride I. To a stirred suspension of 2.84 g. (0.01 mole) of 8-fluoro-5-(p-fluorophenyl)-1,2,3,4-tetrahydro-γ-carboline, 2.8 g. (0.01 mole) of ω-chloro-p-fluorobutyrophenone, 3.15 g. (0.03 mole) of sodium carbonate and a trace (50 mg.) of potassium iodide in 50 ml. of 4-methyl-2-pentanone gave, after heating at reflux for 15 hours followed by work-up of the reaction mixture as described in Preparation C, 2.6 g. of 8-fluoro-5-(p-fluorophenyl)-2-[3-p-fluorobenzoyl)propyl]-1,2,3,4-tetrahydro-γ-carboline free base, M.P. 150°–155° C.

To 846 mg. (22.4 mmole) of sodium borohydride in 50 ml. of ethanol was added dropwise 2.5 g. (5.6 mmoles) of the γ-carboline obtained above in a warm solution of 80 ml. of ethanol and 20 ml. of tetrahydrofuran at such a rate that gentle reflux was maintained. After the addition was completed the mixture was heated at reflux for an additional hour, then cooled to room temperature. The supernatant was decanted into 300 ml. of water and the organic solvents removed from the aqueous phase by evaporation in vacuo. The residue was extracted with dichloromethane and the combined extracts washed with saturated brine and over magnesium sulfate. The solvent was evaporated in vacuo and the residue dissolved in a mixture of ethyl ether and dichloromethane. Hydrogen chloride gas was carefully bubbled into the solution until precipitation ceased. The title compound was recovered by filtration and dried, M.P. 249°–250° C.

PREPARATION E

When 2-carbethoxy-1,2,3,4-tetrahydro-γ-carboline or 8-fluoro-2-carbethoxy-1,2,3,4-tetrahydro-γ-carboline are reacted with o-fluorobromobenzene or m-fluorobromobenzene by the method of Preparation B, Part II and the resulting 5-(o or m-fluorophenyl)-2-carbethoxy-1,2,3,4-tetrahydro-γ-carboline is hydrolyzed and decarboxylated by the procedure of Part III of Preparation B, the following compounds are obtained in like manner.

PREPARATION F 5-(p-Fluorophenyl)-1,2,3,4-tetrahydro-γ-carboline

Equimolar amounts of phenylhydrazine and N-carbethoxy-4-piperidone are reacted by the procedure of Preparation B, Part I, to provide 2-carbethoxy-1,2,3,4-tetrahydro-γ-carboline. This is then reacted with p-fluorobromobenzene according to the procedure of Preparation B, Part II, and the product hydrolyzed by the procedure of Part III of Preparation B to obtain the title compound.

PREPARATION G

8-Fluoro-5-phenyl-1,2,3,4-tetrahydro-γ-carboline

When p-fluorobromobenzene is replaced by an equivalent amount of bromobenzene in Part II of Preparation B and the resulting 2-carbethoxy-8-fluoro-5-phenyl-1,2,3,4-tetrahydro-γ-carboline is hydrolyzed by the procedure of Part III of Preparation B, the title compound is similarly obtained.

PREPARATION H

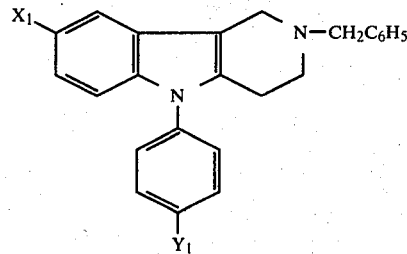

When the product obtained in Preparation F is reacted with benzyl bromide by the procedure of Preparation C, the product obtained is of the above formula wherein $X_1$ is hydrogen and $Y_1$ is fluoro. Similarly, when the product of Preparation G is employed as starting material in the same procedure, a product of the above formula is obtained wherein $X_1$ is fluoro and $Y_1$ is hydrogen.

PREPARATION I

When the products of Preparation E are reacted with benzyl bromide by the procedure of Preparation C, the following compounds are similarly obtained.

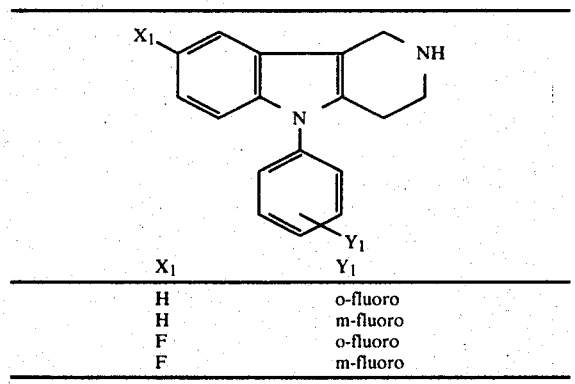

| $X_1$ | $Y_1$ |
|---|---|
| H | o-fluoro |
| H | m-fluoro |
| F | o-fluoro |
| F | m-fluoro |

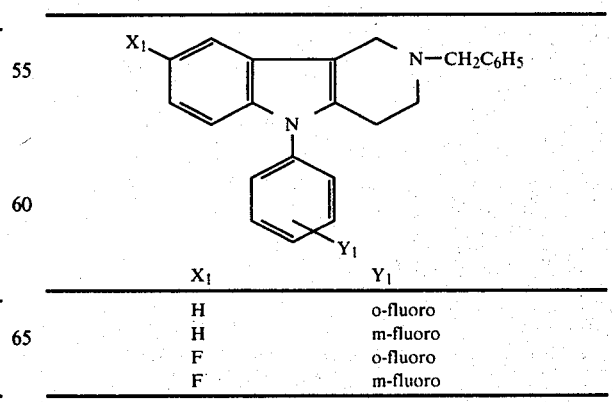

| $X_1$ | $Y_1$ |
|---|---|
| H | o-fluoro |
| H | m-fluoro |
| F | o-fluoro |
| F | m-fluoro |

PREPARATION J

Employing the appropriately substituted 5-phenyl-1,2,3,4-tetrahydro-γ-carboline and $Z_1C_6H_4CO(CH_2)_n\text{-}A$ where A is Cl or Br as starting materials in each case in the procedure of Preparation D, the following compounds are similarly obtained.

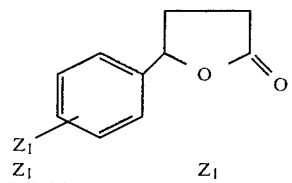

| n | $X_1$ | $Y_1$ | $Z_1$ |
|---|---|---|---|
| 3 | F | p-fluoro | m-fluoro |
| 3 | F | p-fluoro | H |
| 3 | H | p-fluoro | p-methoxy |
| 3 | F | H | o-methoxy |
| 3 | H | H | p-fluoro |
| 4 | F | p-fluoro | p-fluoro |
| 4 | F | p-fluoro | p-methoxy |
| 4 | F | p-fluoro | H |
| 4 | F | H | o-fluoro |
| 4 | F | H | m-methoxy |
| 4 | H | p-fluoro | p-fluoro |
| 4 | H | p-fluoro | H |
| 4 | H | H | H |
| 4 | H | o-fluoro | p-fluoro |
| 3 | H | o-fluoro | p-fluoro |
| 3 | F | o-fluoro | p-fluoro |
| 3 | H | m-fluoro | m-fluoro |
| 3 | F | o-fluoro | p-methoxy |
| 3 | H | m-fluoro | H |
| 4 | F | o-fluoro | o-fluoro |
| 4 | F | m-fluoro | p-methoxy |

PREPARATION K

A mixture of 41 g. (0.25 mole) of 5-hydroxy-5-phenylvaleronitrile, obtained from 4-benzoylbutyronitrile by lithium borohydride reduction by the procedure of Colonge et. al., *Bull. Soc. Chem. France*, 2005-2011 (1966); *Chem. Abstr.*, 65, 18547d (1966), and 0.30 mole of potassium hydroxide in 200 ml. of water was heated at reflux for eight hours. The mixture was cooled to room temperature and neutralized with 10 M hydrochloric acid, saturated with sodium chloride and extracted with ether several times. The extracts were washed with water, dried ($Na_2SO_4$) and the ether evaporated to obtain dl-5-phenyl-5-hydroxyvaleric acid lactone which was recrystallized from dilute alcohol, M.P. 62.5° C., 79% yield.

Employing the appropriate $Z_1$-substituted -5-hydroxy-5-phenylvaleronitrile in the above procedure the analogous compounds of the formula below are also prepared in like manner.

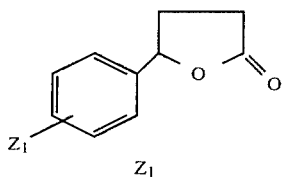

| $Z_1$ | $Z_1$ |
|---|---|
| o-F | o-OCH₃ |
| m-F | m-OCH₃ |
| p-F | p-OCH₃ |

PREPARATION L

To 250 ml. of dry tetrahydrofuran containing 0.10 mole of sodium borohydride is added, dropwise over 45 minutes, a solution of 41.6 g. (0.20 mole) of commercial 3-(p-methoxybenzoyl)propionic acid in the same solvent. After the addition is complete, the reaction mixture is heated at reflux for two hours and cooled to room temperature. The excess borohydride is decomposed by addition of water then washed with water, the organic layer dried ($MgSO_4$) and the solvent evaporated. The residue is taken up in 500 ml. of ethyl acetate and 0.5 g. of p-toluenesulfonic acid is added. The mixture is heated at reflux for 30 minutes, cooled to room temperature, washed with brine and dried ($MgSO_4$). The solvent was evaporated to afford dl-γ-butyrolactone.

Employing the appropriate starting material in the above procedure, the following racemic analogs are prepared in like manner.

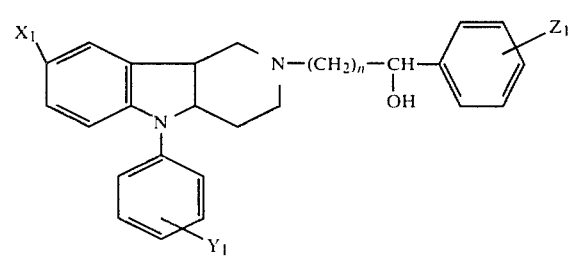

| $Z_1$ |
|---|
| o-OCH₃ |
| m-OCH₃ |
| o-F |
| m-F |

What is claimed is:

1. A process for production of a compound of the formula wherein the hydrogen attached to the carbon atoms in the 4a and 9b positions are in a trans-relationship to each other and $X_1$ and $Y_1$ are the same or different and are each hydrogen or fluoro; $Z_1$ is hydrogen, fluoro or methoxy and n is 3 or 4 which comprises contacting a dextrorotatory or racemic amine of the formula

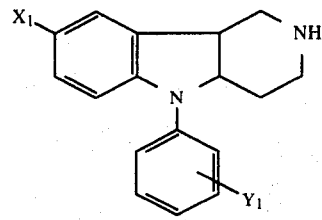

with an equimolar amount of a compound of the formula

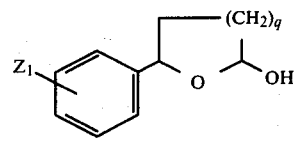

wherein $X_1$, $Y_1$ and $Z_1$ are as previously defined and q is 1 or 2; in the presence of a reaction inert organic solvent and in the presence of a reducing agent, said reducing agent being an equivalent amount of (1) sodium cyanoborohydride or (2) hydrogen and a catalytic amount of noble metal catalyst; at a temperature of from about $-10°$ to 50° C.

2. The process according to claim 1 wherein said noble metal catalyst is platinum or palladium.

3. The process according to claim 2 wherein said catalyst is palladium.

4. The process according to claim 1 wherein said amine is dextrorotatory.

5. The process according to claim 1 wherein n is 3.

6. The process according to claim 5 wherein $X_1$ is fluoro and $Y_1$ and $Z_1$ are each p-fluoro.

* * * * *